United States Patent
Shumway

(10) Patent No.: US 9,655,899 B2
(45) Date of Patent: May 23, 2017

(54) COMPOSITIONS AND METHODS FOR TREATING CANCER

(71) Applicant: Merck Sharp & Dohme Corp., Rahway, NJ (US)

(72) Inventor: Stuart Denham Shumway, Franklin, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/646,518

(22) PCT Filed: Nov. 22, 2013

(86) PCT No.: PCT/US2013/071377
§ 371 (c)(1),
(2) Date: May 21, 2015

(87) PCT Pub. No.: WO2014/085216
PCT Pub. Date: Jun. 5, 2014

(65) Prior Publication Data
US 2016/0008361 A1    Jan. 14, 2016

Related U.S. Application Data

(60) Provisional application No. 61/730,795, filed on Nov. 28, 2012.

(51) Int. Cl.
*A61K 31/519* (2006.01)
*G01N 33/573* (2006.01)
*C12Q 1/68* (2006.01)

(52) U.S. Cl.
CPC .......... *A61K 31/519* (2013.01); *C12Q 1/6886* (2013.01); *G01N 33/573* (2013.01); *C12Q 2600/106* (2013.01); *C12Q 2600/158* (2013.01); *G01N 2333/91011* (2013.01)

(58) Field of Classification Search
None
See application file for complete search history.

(56) References Cited

U.S. PATENT DOCUMENTS

| 5,977,317 A * | 11/1999 | Piwnica-Worms .. C12N 9/1205 530/387.9 |
| 6,020,194 A * | 2/2000 | Mueller ............... C12N 9/1205 435/243 |
| 2011/0092520 A1 | 4/2011 | Furukawa et al. |
| 2012/0172370 A1 | 7/2012 | Petrova et al. |
| 2014/0343071 A1* | 11/2014 | Shumway .............. A61K 45/06 514/252.16 |

FOREIGN PATENT DOCUMENTS

| WO | WO 2011/034743 A1 * | 3/2011 | ........... A61K 31/497 |
| WO | 2012074754 A1 | 6/2012 | |

OTHER PUBLICATIONS

Guertin, A.D.; et al., Preclinical Evaluation of the WEE1 Inhibitor MK-1775 as Single-Agent Anticancer Therapy, Molecular Cancer Therapeutics, 2013, pp. 1442-1452, vol. 12 No. 8.
Tibes, R. et al., RNAi screening of the kinome with cytarabine in leukemias, Blood, 2012, 2863-2872, 119-12.

* cited by examiner

*Primary Examiner* — Peter J Reddig
(74) *Attorney, Agent, or Firm* — Yong Zhao; John C. Todaro

(57) ABSTRACT

The instant invention relates to methods for the treatment of WEE1 kinase associated cancer by administering a WEE1 inhibitor, wherein the WEE1 inhibitor is WEE1-1 or a pharmaceutically acceptable salt thereof, or WEE1-2 or a pharmaceutically acceptable salt thereof. In another embodiment, the invention relates to a method for treating a WEE1 kinase associated cancer patient, comprising administering a WEE1 inhibitor, wherein the cancer cells of said patient to be treated are characterized by low expression levels of PKMYT1.

11 Claims, 10 Drawing Sheets

SEQUENCE LISTING

<160> NUMBER OF SEQ ID NOS: 2

<210> SEQ ID NO 1
<211> LENGTH: 2187
<212> TYPE: DNA
<213> ORGANISM: Homo sapiens

<400> SEQUENCE: 1

| | | | | | |
|---|---|---|---|---|---|
| gagcctcgga | gcccgggcac | ccctgacggg | ctgcactggg | gaggggagg | agcctcgagg | 60 |
| ccggtttgga | attttggcg | cgagcagctc | cgcgcgcgtt | cacgggccgt | tcccctcac | 120 |
| gggagtcctc | cgcccgggcg | tccggaacag | tcgacggcag | actccggccc | gctgagccac | 180 |
| ccgaggggtc | ccgtggcctc | cgcggacccg | gaatctgggc | cctcgcggac | ccgcgccccg | 240 |
| cccagtcgcc | ccagggcttc | cccacaccca | cggagtgaag | tcagccgcgg | ccctgcctgg | 300 |
| gaggaactta | ccgtctaccg | ggaaaggtgg | ccagcagatg | tgtcgggcct | ggtgagaggg | 360 |
| tgaggcgaga | cggcccgatc | gcccagggcc | ccggaagctg | cggaggtcac | cccgcctgg | 420 |
| ccttagctca | gggacaccct | ggattcacgt | gggagcccct | gctcctgcct | ccccgtccc | 480 |
| accactgagg | ctgttgggcc | aggccagtca | tgctagaacg | gcctcctgca | ctggccatgc | 540 |
| ccatgcccac | ggagggcacc | ccgccacctc | tgagtggcac | cccatccca | gtcccagcct | 600 |
| acttccgcca | cgcagaacct | ggattctccc | tcaagaggcc | caggggctc | agccggagcc | 660 |
| tcccacctcc | gccccctgcc | aagggcagca | ttcccatcag | ccgcctcttc | cctcctcgga | 720 |
| ccccaggctg | gcaccagctg | cagccccggc | gggtgtcatt | ccggggcgag | gcctcagaga | 780 |
| ctctgcagag | ccctgggtat | gacccaagcc | ggccagagtc | cttcttccag | cagagcttcc | 840 |
| agaggctcag | ccgcctgggc | catggctcct | acgagaggg | cttcaaggtg | cgctccaagg | 900 |
| aggacggccg | gctctatgcg | gtaaagcgtt | ccatgtcacc | attccggggc | cccaaggacc | 960 |
| gggcccgcaa | gttggccgag | gtgggcagcc | acgagaaggt | ggggcagcac | ccatgctgcg | 1020 |
| tgcggctgga | gcaggcctgg | gaggagggcg | gcatcctgta | cctgcagacg | gagctgtgcg | 1080 |
| ggcccagcct | gcagcaacac | tgtgaggcct | ggggtgccag | cctgcctgag | gcccaggtct | 1140 |
| ggggctacct | gcgggacacg | ctgcttgccc | tggcccatct | gcacagccag | ggcctggtgc | 1200 |
| accttgatgt | caagcctgcc | aacatcttcc | tggggcccg | gggccgctgc | aagctgggtg | 1260 |
| acttcggact | gctggtggag | ctgggtacag | caggagctgg | tgaggtccag | gagggagacc | 1320 |
| cccgctacat | ggcccccgag | ctgctgcagg | gctcctatgg | gacagcagcg | gatgtgttca | 1380 |
| gtctgggcct | caccatcctg | gaagtggcat | gcaacatgga | gctgcccac | ggtggggagg | 1440 |
| gctggcagca | gctgcgccag | ggctacctgc | cccctgagtt | cactgccggt | ctgtcttccg | 1500 |
| agctgcgttc | tgtccttgtc | atgatgctgg | agccagaccc | caagctgcgg | gccacggccg | 1560 |
| aggccctgct | ggcactgcct | gtgttgaggc | agccgcgggc | ctggggtgtg | ctgtggtgca | 1620 |
| tggcagcgga | ggccctgagc | cgagggtggg | ccctgtggca | ggccctgctt | gccctgctct | 1680 |
| gctggctctg | gcatgggctg | gctcaccctg | ccagctggct | acagccctg | ggcccgccag | 1740 |
| ccaccccgcc | tggctcacca | ccctgcagtt | tgctcctgga | cagcagcctc | tccagcaact | 1800 |
| gggatgacga | cagcctaggg | ccttcactct | cccctgaggc | tgtcctggcc | cggactgtgg | 1860 |
| ggagcacctc | caccccccgg | agcaggtgca | cacccaggga | tgccctggac | ctaagtgaca | 1920 |
| tcaactcaga | gcctcctcgg | ggctccttcc | cctcctttga | gcctcggaac | ctcctcagcc | 1980 |
| tgtttgagga | caccctagac | ccaacctgag | ccccagactc | tgcctctgca | cttttaacct | 2040 |
| tttatcctgt | gtctctcccg | tcgcccttga | aagctggggc | ccctcgggaa | ctcccatggt | 2100 |

```
       cttctctgcc tggccgtgtc taataaaaag tatttgaacc ttgggagcac ccaagcttgc    2160
tcatgtggca aaaaaaaaaa aaaaaaa                                        2187
```

<210> SEQ ID NO 2
<211> LENGTH: 499
<212> TYPE: PRT
<213> ORGANISM: Homo sapiens

<400> SEQUENCE: 2

```
Met Leu Glu Arg Pro Pro Ala Leu Ala Met Pro Met Pro Thr Glu Gly
 1               5                  10                  15

Thr Pro Pro Leu Ser Gly Thr Pro Ile Pro Val Pro Ala Tyr Phe
            20                  25                  30

Arg His Ala Glu Pro Gly Phe Ser Leu Lys Arg Pro Arg Gly Leu Ser
        35                  40                  45

Arg Ser Leu Pro Pro Pro Pro Ala Lys Gly Ser Ile Pro Ile Ser
    50                  55                  60

Arg Leu Phe Pro Pro Arg Thr Pro Gly Trp His Gln Leu Gln Pro Arg
65                  70                  75                  80

Arg Val Ser Phe Arg Gly Glu Ala Ser Glu Thr Leu Gln Ser Pro Gly
                85                  90                  95

Tyr Asp Pro Ser Arg Pro Glu Ser Phe Phe Gln Gln Ser Phe Gln Arg
            100                 105                 110

Leu Ser Arg Leu Gly His Gly Ser Tyr Gly Glu Val Phe Lys Val Arg
        115                 120                 125

Ser Lys Glu Asp Gly Arg Leu Tyr Ala Val Lys Arg Ser Met Ser Pro
    130                 135                 140

Phe Arg Gly Pro Lys Asp Arg Ala Arg Lys Leu Ala Glu Val Gly Ser
145                 150                 155                 160

His Glu Lys Val Gly Gln His Pro Cys Cys Val Arg Leu Glu Gln Ala
                165                 170                 175

Trp Glu Glu Gly Gly Ile Leu Tyr Leu Gln Thr Glu Leu Cys Gly Pro
            180                 185                 190

Ser Leu Gln Gln His Cys Glu Ala Trp Gly Ala Ser Leu Pro Glu Ala
        195                 200                 205

Gln Val Trp Gly Tyr Leu Arg Asp Thr Leu Leu Ala Leu Ala His Leu
    210                 215                 220

His Ser Gln Gly Leu Val His Leu Asp Val Lys Pro Ala Asn Ile Phe
225                 230                 235                 240

Leu Gly Pro Arg Gly Arg Cys Lys Leu Gly Asp Phe Gly Leu Leu Val
                245                 250                 255

Glu Leu Gly Thr Ala Gly Ala Gly Glu Val Gln Glu Gly Asp Pro Arg
            260                 265                 270

Tyr Met Ala Pro Glu Leu Leu Gln Gly Ser Tyr Gly Thr Ala Ala Asp
        275                 280                 285

Val Phe Ser Leu Gly Leu Thr Ile Leu Glu Val Ala Cys Asn Met Glu
    290                 295                 300

Leu Pro His Gly Gly Glu Gly Trp Gln Gln Leu Arg Gln Gly Tyr Leu
305                 310                 315                 320

Pro Pro Glu Phe Thr Ala Gly Leu Ser Ser Glu Leu Arg Ser Val Leu
                325                 330                 335

Val Met Met Leu Glu Pro Asp Pro Lys Leu Arg Ala Thr Ala Glu Ala
            340                 345                 350
```

-continued

```
Leu Leu Ala Leu Pro Val Leu Arg Gln Pro Arg Ala Trp Gly Val Leu
        355                 360                 365

Trp Cys Met Ala Ala Glu Ala Leu Ser Arg Gly Trp Ala Leu Trp Gln
    370                 375                 380

Ala Leu Leu Ala Leu Leu Cys Trp Leu Trp His Gly Leu Ala His Pro
385                 390                 395                 400

Ala Ser Trp Leu Gln Pro Leu Gly Pro Pro Ala Thr Pro Pro Gly Ser
                405                 410                 415

Pro Pro Cys Ser Leu Leu Leu Asp Ser Ser Leu Ser Ser Asn Trp Asp
            420                 425                 430

Asp Asp Ser Leu Gly Pro Ser Leu Ser Pro Glu Ala Val Leu Ala Arg
        435                 440                 445

Thr Val Gly Ser Thr Ser Thr Pro Arg Ser Arg Cys Thr Pro Arg Asp
    450                 455                 460

Ala Leu Asp Leu Ser Asp Ile Asn Ser Glu Pro Pro Arg Gly Ser Phe
465                 470                 475                 480

Pro Ser Phe Glu Pro Arg Asn Leu Leu Ser Leu Phe Glu Asp Thr Leu
                485                 490                 495

Asp Pro Thr
```

COMPOSITIONS AND METHODS FOR TREATING CANCER

REFERENCE TO SEQUENCE LISTING SUBMITTED ELECTRONICALLY

The sequence listing of the present application is submitted electronically via EFS-Web as an ASCII formatted sequence listing with a file name "23315USPSP-SEQTXT.txt", creation date of Nov. 28, 2012, and a size of 7078 bytes. This sequence listing submitted via EFS-Web is part of the specification and is herein incorporated by reference in its entirety.

FIELD OF THE INVENTION

The present invention relates generally to the identification of a biomarker whose expression level is useful for predicting a patient's response to treatment with an antiproliferative agent, in particular a WEE1 inhibitor. The expression level of the biomarker can be used to predict a patient presenting with a cancerous condition that is mediated by inhibition of apoptosis and who is likely to respond to treatment with a WEE1 inhibitor.

BACKGROUND OF THE INVENTION

Many commonly used anti-cancer drugs indiscriminately target DNA in dividing cells and ultimately cause DNA damage. This, in turn, triggers activation of cell cycle checkpoints which arrest progression of the cell cycle (at the G1, S, or G2/M phases) with the purpose of allowing time for the DNA to be repaired before the cell undergoes DNA replication or division. From a therapeutic standpoint, inhibition of checkpoint kinases that mediate cell cycle arrest could force tumor cells to continue cell division before chemically-induced DNA damage is repaired, eventually causing apoptosis or mitotic catastrophe (Medema, R. H. and Macurek, L., *Oncogene*, 2012, 31(21):2601-2613). Cell line studies support this hypothesis and show chemosensitization and radiosensitization by pharmacologic or genetic disruption of checkpoint kinase activity including CHK1, WEE1, ATR, and ATM. Inhibitors against these kinases are at various stages of preclinical and clinical development for their ability to sensitize tumor cells to therapeutic DNA damage.

The checkpoint kinase WEE1 catalyzes an inhibitory phosphorylation of both CDK1 (CDC2) and CDK2 on tyrosine 15 (Parker, L. L. and Piwnica-Worms, H., *Science*, 1992, 257(5078):1955-1957; Watanabe, N., et al., *Embo J.*, 1995, 14(9):1878-1891). WEE1-dependent inhibition of CDK1 and CDK2 arrests the cell cycle in response to extrinsically induced DNA damage (Hamer, P. C. D., et al., *Clin. Cancer Res.*, 2011, 17(13):4200-4207). WEE1 activity is also essential for the unperturbed cell cycle (Mcgowan, C. H. and Russell, P., *Embo J.*, 1993, 12(1):75-85; Tominaga, Y., et al., *Intl. J. Biol. Sci.*, 2006, 2(4):161-170). Cell synchronization studies in normal human fibroblasts revealed that similar amounts of WEE1 protein were detected in both S and G2/M phases, but that its greatest activity was in S phase of the cell cycle (Watanabe, N., 1995). Further, upon conditional WEE1 knockout in mouse embryonic fibroblasts (MEFs), cells show evidence of genomic instability, malfunctioning checkpoints, and premature mitosis (Tominaga, et al., 2006). This phenotype was explained in part by recent findings that demonstrate a critical role for WEE1 in DNA synthesis. Knockdown of WEE1, in the absence of DNA damaging agents, led to rapid and robust detection of DNA double strand breaks specifically in S-phase cells undergoing DNA replication (Beck, H., et al., *J. Cell Biol.*, 2010, 188(5):629-638; Dominguez-Kelly, R., et al., *J. Cell Biol.*, 2011, 194(4):567-579). Data support a model of WEE1-dependent genomic stability in which WEE1 knockdown or inhibition leads to aberrantly high activity of CDK 1 and 2, resulting in inappropriately timed firing of excessive DNA replication origins that quickly depletes nucleotide pools and leads to stalled replication forks which, in the absence of WEE1 activity, are substrates for DNA exonucleases and resolve into DNA doubles strand breaks (Beck, H., et al., 2012).

Deregulated WEE1 expression or activity is believed to be a hallmark of pathology in several types of cancer. WEE1 is often overexpressed in glioblastomas and its activity protects this tumor type from mitotic catastrophe such that high WEE1 levels are associated with poor prognosis (Mir, S. E., et al., *Cancer Cell*, 2010, 18(3):244-257). High expression of WEE1 was found in malignant melanoma and correlated with poor disease-free survival in this population (Magnussen, G. I., et al., *Plos One*, 2012, 7(6)). Aberrant WEE1 expression has been implicated in additional tumor types such as hepatocellular carcinoma (Masaki, T., et al., *Hepatology*, 2003, 37(3):534-543), breast cancer (Iorns, E., et al., *Plos One*, 2009, 4(4)), colon carcinoma (Backert, S., et al., *Intl., J. Cancer*, 1999, 82(6):868-874)), lung carcinoma (Yoshida, T., et al., *Annals of Oncology*, 2004, 15(2): 252-256) and head and neck squamous cell carcinoma (Wu, Z. X., et al., *Mol. & Cell. Proteomics*, 2011, 10(12)). Advanced tumors with an increased level of genomic instability may require functional checkpoints to allow for repair of such lethal DNA damage. As such, WEE1 represents an attractive target in advanced tumors where its inhibition is believed to result in irreparable DNA damage (Sorensen, C. S. and Syljuasen, R. G., *Nuc. Acids Res.*, 2012, 40(2):477-486).

There is a need for biomarkers that can be used to predict which patients are amenable to treatment with specific therapies, particularly for patients who are non-responsive or who are likely to become refractive to first line therapies. It is, therefore, an object of this invention to provide a predictive biomarker to select patients likely to respond to treatment with a WEE1 inhibitor.

SUMMARY OF THE INVENTION

The instant invention relates generally to the identification of a predictive biomarker whose expression level is useful for evaluating and classifying patients for treatment with a WEE1 inhibitor. In one embodiment of the invention the predictive biomarker, PKMYT1, is used to identify patients likely to respond to treatment with a WEE1 inhibitor, wherein the WEE1 inhibitor is WEE1-1. In another embodiment, the invention is a method for treating a patient diagnosed with a WEE1 associated cancer with a WEE1 inhibitor, wherein the cancer cells of said patient are characterized by low expression of PKMYT1. In still another embodiment, the invention is a method for treating a cancer patient who is sensitive to treatment with a WEE1 inhibitor, wherein the cancer cells of said patient are characterized by a level of expression of PKMYT1 that is below that of a reference value. In another embodiment, the invention is a method to identify WEE1 inhibitors for use in treating a WEE1 kinase associated cancer. In yet another embodiment, the invention is a kit for identifying patients likely to respond to treatment with a WEE1 inhibitor comprising reagents reacting to PKMYT1.

BRIEF DESCRIPTION OF THE DRAWINGS

In FIGS. 3A and 3B, cells were stimulated to resume cycling with 20% FBS in the added presence of either vehicle (DMSO) in lanes 1-6 or 500 nM WEE1-1 in lanes 7-11. Time of harvest following FBS stimulation is indicated. One hour prior to harvest, cells were pulse-labeled with BrdU and the percentage of BrdU-staining cells is shown in the top panel. Protein lysates from ES-2 cells treated in parallel were collected followed by Western blotting with the indicated antibodies. In comparison to vehicle-treated control, WEE1-1 treatment delays progression through S phase (FIG. 3A, top panel, and FIG. 3B) and S phase BrdU uptake (FIG. 3A, top panel), indicating a slowing of DNA replication. WEE1-1 treatment delays cyclin A expression and induces DNA damage signaling as evidenced by $pChk1^{S345}$ (FIG. 3A, bottom left panel). FIG. 3B shows the flow cytometry analysis in select samples (4, 12, and 24 hour treatments) from part A comparing BrdU-staining and DNA content. Data in FIG. 3C are representative of serum-starved ES-2 cells to which 500 nM WEE1-1 was added in either the presence or absence of 20% FBS. Twenty-four hours later, DNA content and γH2AX (DNA double strand breaks) were analyzed by flow cytometry. Percentages of the total population of cells are given in the chart (FIG. 3C), demonstrating that WEE1-1 induces DNA double strand breaks in more cells when the population is stimulated by 20% FBS.

FIG. 5B shows the final tumor volume of individual A427 xenografts treated for 28 days with either vehicle or MK-1775 were plotted. Mean tumor volume at the start of the study was 164 $mm^3$ and is indicated by a dashed line. FIGS. 5C and 5D illustrate additional in vivo efficacy studies carried out in SK-MES-1 (C) and LoVo (D) xenograft models as described for FIG. 5A with the exception that WEE1-1 treatment stopped on day 13 in the LoVo xenograft study (indicated by an asterisk) and tumor volumes were measured for an additional 2 weeks.

FIG. 6A illustrates that PKMYT1 was knocked down in two cell lines that display relative WEE1-1 resistance, H460 and KNS62. Cells were transfected with siRNA pools containing non-targeting control (CT) or PKMYT1 sequences. Cells were treated with WEE1-1, carboplatin, a MEK inhibitor (PD0325901), or doxorubicin for 72 hours prior to assaying for proliferation with the ViaLight ATP assay. Knockdown of PKMYT1 lowered the proliferation $EC_{50}$ for WEE1-1 alone, but not for the other compounds tested. In FIG. 6B KNS62 cells were transfected with non-targeting control (CT) or PKMYT1 siRNA pools and treated with 400 nM WEE1-1 for the indicated times.

In FIG. 7A relative PKMYT1 expression (CCLE database, Broad-Novartis) was plotted against response to 400 nM WEE1-1 treatment in 305 cell lines, each represented by a single dot. The response to WEE1-1 (x-axis) is an adjusted value based on a 96-hour proliferation assay where a value of 1 indicates no change in growth rate relative to DMSO treated cells and a value of 0.25 (vertical dashed line) or less indicates a negative growth rate, or cell death. Mean relative PKMYT1 expression among the 305 cell lines is 413. FIG. 7B illustrates the proliferative response to WEE1-1, measured in $EC_{50}$ values (μM), plotted against relative expression of PKMYT1 mRNA (left panel) or PKMYT1 protein (right panel) for thirteen cell lines not included in the analysis in FIG. 7A above.

In FIG. 8A lysates were probed with individual antibodies against the WEE1 substrate ($pCDK1^{Y15}$), DDR marker ($pCHK1^{S345}$), or CDK1 and 2 substrates ($pStathmin^{S38}$ and $pLaminA/C^{S22}$, respectively). In FIG. 8B lysates were probed with a pan CDK-substrate motif antibody.

FIG. 9A illustrates a histogram of the cell cycle distribution. FIG. 9B illustrates a scatter plot with gates that indicates the γH2AX population. The percentage of total cells is indicated in either the cell cycle phase or as γH2AX positive.

DETAILED DESCRIPTION OF THE INVENTION

Figure 1:
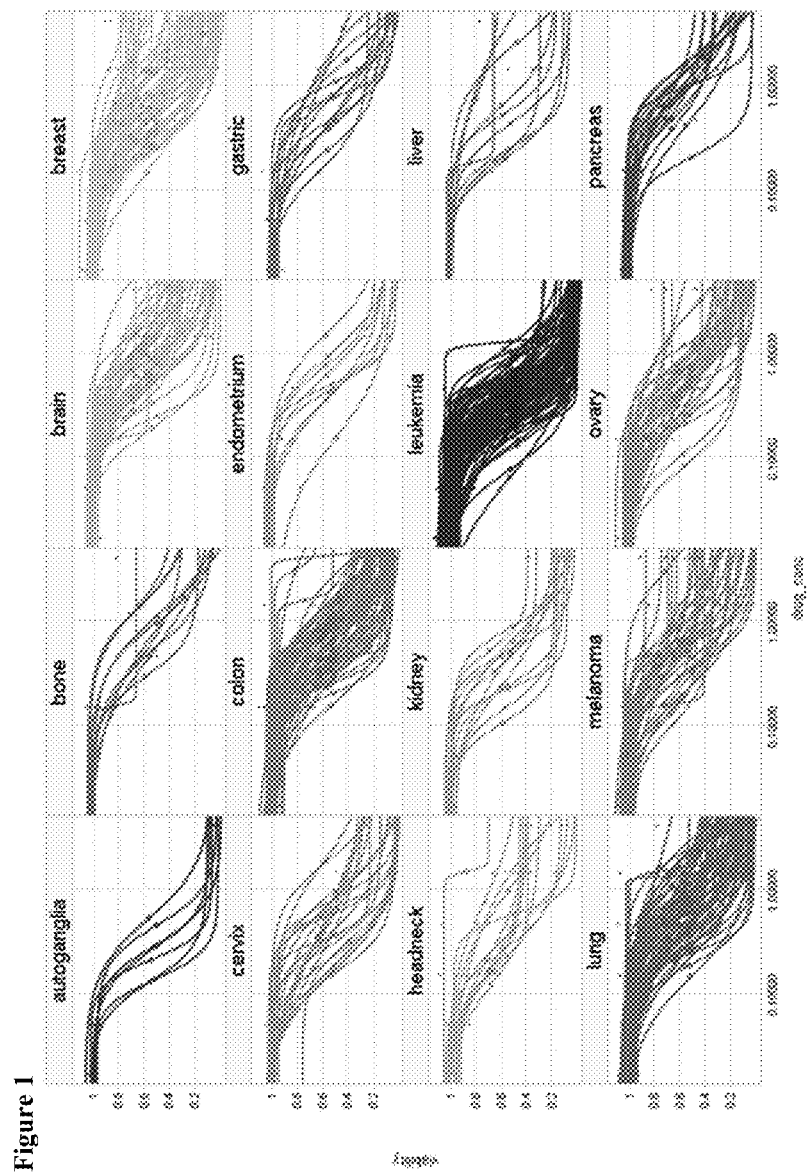
FIG. 1 is a graphic illustration of the disruption of cellular proliferation in diverse tumor cell lines by a WEE1 inhibitor. Proliferation over a 96-hour window was assayed in triplicate for 522 cancer cell lines treated with 9-point titration of WEE1-1. Cell line response data is broken down into tumor tissue of origin and represented as fractional viability (relative to DMSO-treated control cells) as a function of WEE1-1 concentration.

Many anti-cancer treatments act by damaging DNA, which subsequently initiates the DNA damage response (DDR) and activates checkpoint kinases to arrest division while the DNA is repaired. WEE1, a tyrosine kinase, is activated by the DDR to phosphorylate and inhibit cyclin dependent kinases (CDKs) 1 and 2 and, as such, arrest cell division Inhibiting WEE1 potentiates DNA damaging treatments by abrogating cell cycle arrest and proper DNA repair.

WEE1-1, also known as 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one, is a potent ($IC_{50}$=5.2 nM) and selective ATP-competitive small molecule inhibitor of WEE1 (Hirai, H., et al., *Mol. Cancer Ther.*, 2009, 8(11):2992-3000) that is currently under clinical development as an anti-tumor agent in combination with standard of care (SOC) chemotherapeutics (Stathis, A. and Oza A., *Drug News & Perspectives*, 2010, 23(7):425-429; Schellens, J. H. M., et al., *J. Clin. Oncol.*, 2011, 29:2011 (suppl; abstr 3068); Mizuarai, S., et al., *Mol. Cancer*, 2009, 8:34). Previous studies on WEE1-1 have demonstrated its potential as an adjunct or sensitizer to currently used standard of care (SOC) chemotherapeutics by its ability to force unscheduled mitosis that ultimately results in apoptosis or mitotic catastrophe (Hirai, H., et al., *Cancer Biol. & Ther.*, 2010, 9(7):514-522; Aarts, M., et al., *Cancer Discovery*, 2012, 2(6):524-539; Indovina, P. and Giordano A., *Cancer Biol. & Ther.*, 2010, 9(7); 523-525; Wang, Y. L., et al., *Cancer Biol. & Ther.*, 2004, 3(3):305-313). However, the potential therapeutic effect of WEE1 inhibition in the absence of SOC chemotherapy is less defined. RNAi knockdown of WEE1 inhibited proliferation of cancer cell lines (Iorns, E., et al., *Cancer Targets*, 2009, Plos One, 4(4); Murrow, L. M., et al., *Breast Cancer Research and Treatment*, 2010, 122(2):347-357) and recently it was demonstrated that WEE1-1 alone can induce apoptosis in sarcoma cell lines treated in vitro (Kreahling, J. M., et al., *Mol. Cancer Ther.*, 2012, 11(1):174-182).

Applicants herein demonstrate that pharmacologic inhibition of WEE1 alone, through the use of WEE1-1 as a single agent, was cytotoxic across a broad panel of tumor cell lines and strongly induced DNA double strand breaks. Notably, WEE1-1 induced DNA damage that was independent of SOC chemotherapy or radiotherapy, that occurred in S-phase cells, and that relied upon active DNA replication. At tolerated doses, WEE1-1 single agent therapy lead to xenograft tumor growth inhibition or regression. Knockdown of PKMYT1, a kinase functionally related to WEE1, selectively sensitized cancer cells to WEE1-1, but did not sensitize them to other cytotoxic agents. As described herein, expression of PKMYT1 was below average in roughly three quarters of the cancer cell lines most responsive to WEE1-1. Selecting cell lines that had low PKMYT1 expression levels was predictive of the in vitro sensitivity of these cell lines to WEE1-1. Taken together, these findings provide the basis for the use of WEE1 inhibition as a potent single agent anti-cancer therapy and the use of low PKMYT1 expression to identify and select patients most likely to respond to WEE1-1 single agent therapy.

Accordingly, the instant invention relates to methods for treating cancer with a WEE1 inhibitor, wherein the WEE1 inhibitor is WEE1-1 or a pharmaceutically acceptable salt thereof, or WEE1-2 or a pharmaceutically acceptable salt thereof. In another embodiment, the invention relates to a predictive biomarker, PKMYT1, whose expression is sensitive to WEE1 inhibition by a WEE1 inhibitor. In still another embodiment, the invention relates to a method for treating a patient diagnosed with a WEE1 kinase associated cancer, in need of treatment thereof, with a WEE1 inhibitor, wherein the cancer cells of said patient are characterized by low expression of PKMYT1, and wherein said WEE1 inhibitor is WEE1-1 or a pharmaceutically acceptable salt thereof, or WEE1-2 or a pharmaceutically acceptable salt thereof. In yet another embodiment, the invention is a method for treating a cancer patient who is sensitive to treatment with a WEE1 inhibitor, wherein the cancer cells of said patient are characterized by a level of expression of PKMYT1 that is below that of a reference value, and wherein said WEE1 inhibitor is WEE1-1 or a pharmaceutically acceptable salt thereof, or WEE1-2 or a pharmaceutically acceptable salt thereof. In another embodiment, the invention is a method to identify PKMYT1 inhibitors for use in treating a WEE1 kinase associated cancer. In yet another embodiment, the invention is a kit for identifying patients likely to respond to treatment with a WEE1 inhibitor comprising reagents reacting to PKMYT1.

In an embodiment of the invention, the WEE1 inhibitor is WEE1-1 or a pharmaceutically acceptable salt thereof.

In another embodiment of the invention, the WEE1 inhibitor is administered in a dose between 100 mg per day and 200 mg per day. In an embodiment of the invention, the WEE1 inhibitors may be dosed twice a day (BID) over the course of two and a half days (for a total of 5 doses) or once a day (QD) over the course of two days (for a total of 2 doses).

The term "cancer" as referred to in this description includes various sarcoma and carcinoma and includes solid cancer and hematopoietic cancer. The solid cancer as referred to herein includes, for example, brain cancer, cervicocerebral cancer, esophageal cancer, thyroid cancer, small cell lung cancer, non-small cell lung cancer, breast cancer, endometrial cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' tumor, skin cancer, malignant melanoma, neuroblastoma, osteosarcoma, Ewing's tumor, soft part sarcoma. On the other hand, the hematopoietic cancer includes, for example, acute leukemia, chronic lymphatic leukemia, chronic myelocytic leukemia, polycythemia vera, malignant lymphoma, multiple myeloma, Hodgkin's lymphoma, non-Hodgkin's lymphoma.

The term "WEE1 kinase associated cancer" as referred to in this description means a cancer associated with the activity or inhibition of WEE1 kinases including, but not limited to, brain cancer, cervicocerebral cancer, esophageal cancer, thyroid cancer, small cell cancer, non-small cell cancer, breast cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' cancer, skin cancer, malignant melanoma, neuroblastoma, osteosarcoma, Ewing's tumor, soft part sarcoma, acute leukemia, chronic lymphatic leukemia, chronic myelocytic leukemia, Hodgkin's lymphoma, or as sensitizers for chemo therapy or radiation therapy of those cancers. In particular, the WEE1 inhibitor of the invention are useful as remedies, for example, for breast cancer, lung cancer, pancreatic cancer, colon cancer, ovarian cancer, acute leukemia, chronic lymphatic leukemia, chronic myelocytic leukemia, Hodgkin's lymphoma, or as sensitizers for chemotherapy or radiation therapy of those cancers.

The term "treatment of cancer" as referred to in this description means that an anti-cancer agent is administered to a cancer patient so as to inhibit the growth of the cancer cells in the patient. Preferably, the treatment results in some form of cancer growth regression or that the treatment delays or prevents the recurrence of the cancer. More preferably, the treatment results in complete disappearance of cancer.

The term "patient" or "subject" as referred to in this description means the recipient in need of medical intervention or treatment. Mammalian and non-mammalian patients or subjects are included.

The term "predictive biomarker" as referred to in this description means a gene marker whose expression is correlated with a response to a given therapeutic agent or class of therapeutic agents. As used herein, the term refers to PKMYT1, whose expression is correlated with the therapeutic effect of a WEE1 inhibitor. In one embodiment herein, the WEE1 inhibitor is WEE1-1.

"Marker-derived polynucleotides" means the RNA transcribed from a marker gene, any cDNA or cRNA produced there from, and any nucleic acid derived there from, such as synthetic nucleic acid having a sequence derived from the gene corresponding to the marker gene.

The terms "control," "control level," "reference level," or "pre-determined reference level" means a separate baseline level measured in a comparable control cell, which may or may not be disease free. It may be from the same individual or from another individual who is normal or does not present with the same disease from which the disease or test sample is obtained. Thus, "reference value" can be an absolute value, a range of values, an average value, a median value, a mean value, or a value as compared to a particular control or baseline value. A reference value can be based on an individual sample value, such as, a value obtained from a sample from an individual with a WEE1 kinase associated cancer, but at an earlier point in time or prior to treatment, or a value obtained from a sample from a patient diagnosed with a WEE1 kinase associated cancer other than the individual being tested, or a "normal" individual, that is an individual not diagnosed with a WEE1 kinase associated cancer. The reference value can be based on a number of samples, such as from multiple patients diagnosed with a WEE1 kinase mediated cancer, or normal individuals, or based on a pool of samples including or excluding the sample to be tested.

The term "PKMYT1" as referred to in this description means the gene that encodes the membrane-associated tyrosine- and threonine-specific CDK1 inhibitory kinase, a protein that is a member of the serine/threonine protein kinase family (Liu, F., et al., *Mol. Cell. Biol.*, 1997, 17(2):571-583, the sequence of which is set forth in NCBI Reference Sequence Numbers NM_004203 (SEQ ID NO: 1) and NP_004194 (SEQ ID NO: 2).

The term "low expression of PKMYT1" or "low PKMYT1 expression" as referred to in this description means a cell, obtained from a cell line characterized as or from a patient diagnosed with cancer, having lower PKMYT1 DNA, mRNA, or protein expression, or a decrease in the number of copies of the PKMYT1 gene, as compared to a cell, obtained from a cell line characterized as or from a patient not diagnosed with cancer, or a control cell.

As used herein, the terms "measuring expression levels," "measuring gene expression level," or "obtaining an expression level" and the like, includes methods that quantify target gene expression level exemplified by a transcript of a gene, including microRNA (miRNA) or a protein encoded by a gene, as well as methods that determine whether a gene of interest is expressed at all. Thus, an assay which provides a "yes" or "no" result without necessarily providing quantification of an amount of expression is an assay that "measures expression" as that term is used herein. Alternatively, the term may include quantifying expression level of the target gene expressed in a quantitative value, for example, a fold-change in expression, up or down, relative to a control gene or relative to the same gene in another sample, or a log ratio of expression, or any visual representation thereof, such as, for example, a "heatmap" where a color intensity is representative of the amount of gene expression detected. Exemplary methods for detecting the level of expression of a gene include, but are not limited to, Northern blotting, dot or slot blots, reporter gene matrix (see, for example, U.S. Pat. No. 5,569,588), nuclease protection, RT-PCR, microarray profiling, differential display, SAGE (Velculescu et al., (1995), *Science* 270:484-87), Digital Gene Expression System (see WO2007076128; WO2007076129), multiplex mRNA assay (Tian et al., (2004), *Nucleic Acids Res.* 32:e126), PMAGE (Kim et al., (2007), *Science* 316:1481-84), cDNA-mediated annealing, selection, extension and ligation assay (DASL, Bibikova, et al., (2004), *AJP* 165:1799-807), multiplex branched DNA assay (Flagella et al., (2006), *Anal. Biochem.* 352:50-60), 2D gel electrophoresis, SELDI-TOF, ICAT, enzyme assay, antibody assay, and the like.

WEE1 Inhibitors

In an embodiment of the invention, the WEE1 inhibitor of the instant invention is WEE1-1, the structure of which is as shown below.

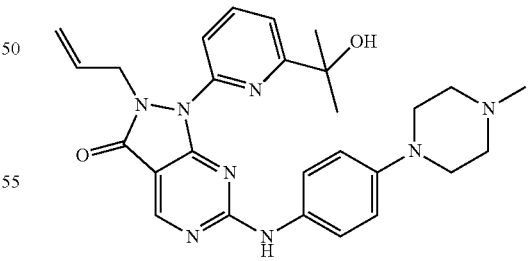

WEE1-1

WEE1-1 is a WEE1 inhibitor which is useful for the treatment of cancer. WEE1-1 is also known as 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one. WEE1-1 has been described in U.S. Pat. No. 7,834,019, and in PCT International Publication WO2007/126122, WO 2007/126128 and WO2008/153207, which are incorporated by reference herein in their entirety.

Crystalline forms of WEE1-1 are described in US Publication US2010-0124544 and PCT International Publication WO2011/034743, which are incorporated by reference herein in their entirety.

In an embodiment of the invention, the WEE1 inhibitor of the instant invention is WEE1-2, the structure of which is as shown below.

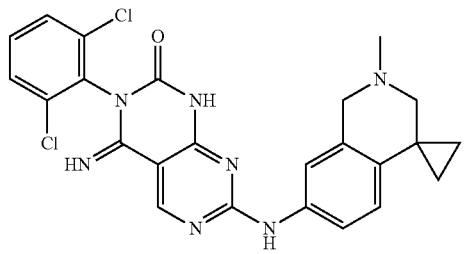

WEE1-2

WEE1-2 is a WEE1 inhibitor which is useful for the treatment of cancer. WEE1-2 is also known as 3-(2,6-dichlorophenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one. WEE1-2 has been described in PCT International Publication WO2008/153207 and US Publication US2011-0135601, which are incorporated by reference herein in their entirety. Crystalline forms of WEE1-2 are described in International Publication WO2009/151997 and US Publication US2011-0092520

The compounds of the present invention may have asymmetric centers, chiral axes, and chiral planes (as described in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted.

In the compounds described in the present invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds disclosed herein. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds disclosed herein can be prepared without undue experimentation by conventional techniques well known to those skilled in the art or by processes analogous to those described in the Schemes and Examples herein using appropriate isotopically-enriched reagents and/or intermediates.

The WEE1 inhibitors of the instant invention may also exist as various crystals, amorphous substances, pharmaceutically acceptable salts, hydrates and solvates. Further, the WEE1 inhibitors of the instant invention may be provided as prodrugs. In general, such prodrugs are functional derivatives of the WEE1 inhibitors of the instant invention that can be readily converted into compounds that are needed by living bodies. Accordingly, in the method of treatment of various cancers in the invention, the term "administration" includes not only the administration of a specific compound but also the administration of a compound which, after administered to patients, can be converted into the specific compound in the living bodies. Conventional methods for selection and production of suitable prodrug derivatives are described, for example, in "Design of Prodrugs", ed. H. Bundgaard, Elsevier, 1985, which is referred to herein and is entirely incorporated herein as a part of the present description. Metabolites of the compound may include active compounds that are produced by putting the compound in a biological environment, and are within the scope of the compound in the invention.

Determination of Biomarker Expression Levels

A. Methods of Measuring a Biomarker

In one embodiment the invention is a predictive biomarker, PKMYT1, whose expression is sensitive to WEE1 inhibition by a WEE1 inhibitor. The expression levels of the predictive biomarker in a sample may be determined by any means known in the art. The expression level may be determined by isolating and determining the level (i.e., amount) of nucleic acid transcribed from the biomarker. Alternatively, or additionally, the level of specific proteins encoded by the biomarker may be determined.

The level of expression of a biomarker can be accomplished by determining the amount of mRNA, or polynucleotides derived therefrom, present in a sample. Any method for determining RNA levels can be used. For example, RNA is isolated from a sample and separated on an agarose gel. The separated RNA is then transferred to a solid support, such as a filter. Nucleic acid probes representing one or more markers are then hybridized to the filter by northern hybridization, and the amount of marker-derived RNA is determined. Such determination can be visual, or machine-aided, for example, by use of a densitometer. Another method of determining RNA levels is by use of a dot-blot or a slot-blot. In this method, RNA, or nucleic acid derived therefrom, from a sample is labeled. The RNA or nucleic acid derived therefrom is then hybridized to a filter containing oligonucleotides derived from one or more marker genes, wherein the oligonucleotides are placed upon the filter at discrete, easily-identifiable locations. Hybridization, or lack thereof, of the labeled RNA to the filter-bound oligonucleotides is determined visually or by densitometer. Polynucleotides can be labeled using a radiolabel or a fluorescent (i.e., visible) label.

The expression of a biomarker gene in a number of tissue specimens may be characterized using a "tissue array" (Kononen et al., Nat. Med, 1998, 4(7):844-847). In a tissue array, multiple tissue samples may be assessed on the same microarray. The tissue array allow in situ detection of RNA and protein levels; consecutive sections allow the analysis of multiple samples simultaneously.

These examples are not intended to be limiting, as other methods of determining RNA abundance are known in the art.

B. Microarrays

In some embodiments, polynucleotide microarrays may be used to measure expression so that the expression status of each biomarker is assessed simultaneously. When this method of measurement is used, the microarray preferably comprises at least 2, 3, 4, 5 or more biomarkers, or all of the biomarkers, or any combination of biomarkers, identified as classification-informative within a subject subset. The actual number of informative biomarkers the microarray comprises will vary depending upon the particular condition of interest, the number of biomarkers identified, and, optionally, the number of informative biomarkers found to result in the least Type I error, Type II error, or Type I and Type II error in determination of an endpoint phenotype. As used herein, "Type I error" means a false positive and "Type II error" means a false negative; in the example of predicting a patient's therapeutic response to exposure to a CDK inhibitor, Type I error is the mischaracterization of an individual with a therapeutic response to a CDK inhibitor as being a non-responsive to CDK inhibitor treatment, and Type II error is the mischaracterization of an individual with no response to CDK inhibitor treatment as having a therapeutic response.

When used in a specific embodiment, the invention provides polynucleotide arrays in which the biomarkers identified for a particular subject subset comprise at least 50%, 60%, 70%, 80%, 85%, 90%, 95% or 98% of the probes on said array. In another specific embodiment, the microarray comprises a plurality of probes, wherein said plurality of probes comprise probes complementary and hybridizable to at least 75% of the WEE1 inhibitor exposure/prediction-informative biomarkers identified for a particular patient subset. Microarrays of the invention, of course, may comprise probes complementary to and which are capable of hybridizing to WEE1 inhibitor prediction/evaluation-informative biomarkers for a plurality of the subject subsets, or for each subject subset, identified for a particular condition. In furtherance thereof, a microarray of the invention comprises a plurality of probes complementary to and which hybridize to at least 75% of the WEE1 inhibitor prediction/evaluation-informative biomarkers identified for each subject subset identified for the condition of interest, and wherein said probes, in total, are at least 50% of the probes on said microarray.

In yet another specific embodiment, the microarray is a commercially-available cDNA microarray that comprises at least two biomarkers identified by the methods described herein. Preferably, a commercially-available cDNA microarray comprises all of the biomarkers identified by the methods described herein as being informative for a patient subset for a particular condition. However, such a microarray may comprise at least 1, 2, 3, 4 or 5 of such markers, up to the maximum number of markers identified.

Any of the microarrays described herein may be provided in a sealed container in a kit.

C. Polynucleotides Used to Measure the Products of the Predictive Biomarker

Polynucleotides capable of specifically or selectively binding to the mRNA transcripts encoding the polypeptide predictive biomarker, PKMYT1, of the invention are also contemplated. For example: oligonucleotides, cDNA, DNA, RNA, PCR products, synthetic DNA, synthetic RNA, or other combinations of naturally occurring or modified nucleotides which specifically and/or selectively hybridize to one or more of the RNA products of the predictive biomarker of the invention are useful in accordance with the invention.

In a preferred embodiment, the oligonucleotides, cDNA, DNA, RNA, PCR products, synthetic DNA, synthetic RNA, or other combinations of naturally occurring or modified nucleotides oligonucleotides which both specifically and selectively hybridize to one or more of the RNA products of the predictive biomarker of the invention are used.

To determine the (high or low) expression level of PKMYT1 in the practice of the present invention, any method known in the art may be utilized. In one embodiment of the invention, expression based on detection of RNA which hybridizes to the gene identified and disclosed herein is used. This is readily performed by any RNA detection or amplification methods known or recognized as equivalent in the art such as, but not limited to, reverse transcription-PCR, and methods to detect the presence, or absence, of RNA stabilizing or destabilizing sequences.

Alternatively, expression based on detection of DNA status may be used. Detection of the DNA of an identified gene as may be used for genes that have increased expression in correlation with a particular outcome. This may be readily performed by PCR based methods known in the art, including, but not limited to, Q-PCR. Conversely, detection of the DNA of an identified gene as amplified may be used for genes that have increased expression in correlation with a particular treatment outcome. This may be readily performed by PCR based, fluorescent in situ hybridization (FISH) and chromosome in situ hybridization (CISH) methods known in the art.

D. Techniques to Measure the RNA Products of a Biomarker

1. Real-Time PCR

In practice, a gene expression-based expression assay based on a small number of genes, i.e., about 1 to 3000 genes can be performed with relatively little effort using existing quantitative real-time PCR technology familiar to clinical laboratories. Quantitative real-time PCR measures PCR product accumulation through a dual-labeled fluorigenic probe. A variety of normalization methods may be used, such as an internal competitor for each target sequence, a normalization gene contained within the sample, or a housekeeping gene. Sufficient RNA for real time PCR can be isolated from low milligram quantities from a subject. Quantitative thermal cyclers may now be used with microfluidics cards preloaded with reagents making routine clinical use of multigene expression-based assays a realistic goal.

The gene markers of the inventive predictive biomarker or a subset thereof, which are assayed according to the present invention, are typically in the form of total RNA or mRNA or reverse transcribed total RNA or mRNA. General methods for total and mRNA extraction are well known in the art and are disclosed in standard textbooks of molecular biology, including Ausubel et al., *Current Protocols of Molecular Biology*, John Wiley and Sons (1997). RNA isolation can also be performed using purification kit, buffer set and protease from commercial manufacturers, such as Qiagen (Valencia, Calif.) and Ambion (Austin, Tex.), according to the manufacturer's instructions.

TAQman quantitative real-time PCR can be performed using commercially available PCR reagents (Applied Biosystems, Foster City, Calif.) and equipment, such as ABI Prism 7900HT Sequence Detection System (Applied Biosystems) according the manufacturer's instructions. The system consists of a thermocycler, laser, charge-coupled device (CCD), camera, and computer. The system amplifies samples in a 96-well or 384-well format on a thermocycler. During amplification, laser-induced fluorescent signal is collected in real-time through fiber-optics cables for all 96 wells, and detected at the CCD. The system includes software for running the instrument and for analyzing the data.

Based upon the predictive biomarker identified in the present invention, a real-time PCR TAQman assay can be used to make gene expression measurements and perform the classification methods described herein. As is apparent to a person of skill in the art, a wide variety of oligonucleotide primers and probes that are complementary to or hybridize to the predictive biomarker of the invention may be selected based upon the predictive biomarker transcript sequence.

2. Array Hybridization

The polynucleotide used to measure the RNA products of the invention can be used as nucleic acid members stably associated with a support to comprise an array according to one aspect of the invention. The length of a nucleic acid member can range from 8 to 1000 nucleotides in length and are chosen so as to be specific for the RNA products of the predictive biomarker of the invention. In one embodiment, these members are selective for the RNA products of the invention. The nucleic acid members may be single or double stranded, and/or may be oligonucleotides or PCR fragments amplified from cDNA. Preferably oligonucleotides are approximately 20-30 nucleotides in length. ESTs are preferably 100 to 600 nucleotides in length. It will be understood to a person skilled in the art that one can utilize portions of the expressed regions of the predictive biomarker of the invention as a probe on the array. More particularly oligonucleotides complementary to the genes of the invention and cDNA or ESTs derived from the genes of the invention are useful. For oligonucleotide based arrays, the selection of oligonucleotides corresponding to the gene of interest which are useful as probes is well understood in the art. More particularly it is important to choose regions which will permit hybridization to the target nucleic acids. Factors such as the Tm of the oligonucleotide, the percent GC content, the degree of secondary structure and the length of nucleic acid are important factors. See for example U.S. Pat. No. 6,551,784.

3. Construction of a Nucleic Acid Array

In the proposed methods, an array of nucleic acid members stably associated with the surface of a substantially support is contacted with a sample comprising target nucleic acids under hybridization conditions sufficient to produce a hybridization pattern of complementary nucleic acid members/target complexes in which one or more complementary nucleic acid members at unique positions on the array specifically hybridize to target nucleic acids. The identity of target nucleic acids which hybridize can be determined with reference to location of nucleic acid members on the array.

The nucleic acid members may be produced using established techniques such as polymerase chain reaction (PCR) and reverse transcription (RT). These methods are similar to those currently known in the art (see, for example, *PCR Strategies*, Michael A. Innis (Editor), et al., 1995 and *PCR: Introduction to Biotechniques Series*, C. R. Newton, A. Graham, 1997). Amplified nucleic acids are purified by methods well known in the art (e.g., column purification or alcohol precipitation). A nucleic acid is considered pure when it has been isolated so as to be substantially free of primers and incomplete products produced during the synthesis of the desired nucleic acid. Preferably, a purified nucleic acid will also be substantially free of contaminants which may hinder or otherwise mask the specific binding activity of the molecule.

An array, according to one aspect of the invention, comprises a plurality of nucleic acids attached to one surface of a support at a density exceeding 20 different nucleic acids/$cm^2$, wherein each of the nucleic acids is attached to the surface of the support in a non-identical pre-selected region (e.g. a microarray). Each associated sample on the array comprises a nucleic acid composition, of known identity, usually of known sequence, as described in greater detail below. Any conceivable substrate may be employed in the invention.

In one embodiment, the nucleic acid attached to the surface of the support is DNA. In one embodiment, the nucleic acid attached to the surface of the support is cDNA or RNA. In another embodiment, the nucleic acid attached to the surface of the support is cDNA synthesized by polymerase chain reaction (PCR). Usually, a nucleic acid member in the array, according to the invention, is at least 10, 25, 50, 60 nucleotides in length. In one embodiment, a nucleic acid member is at least 150 nucleotides in length. Preferably, a nucleic acid member is less than 1000 nucleotides in length. More preferably, a nucleic acid member is less than 500 nucleotides in length.

In the arrays of the invention, the nucleic acid compositions are stably associated with the surface of a support, where the support may be a flexible or rigid support. By "stably associated" is meant that each nucleic acid member maintains a unique position relative to the support under hybridization and washing conditions. As such, the samples are non-covalently or covalently stably associated with the support surface. Examples of non-covalent association include non-specific adsorption, binding based on electrostatic interactions (e.g., ion pair interactions), hydrophobic interactions, hydrogen bonding interactions, specific binding through a specific binding pair member covalently attached to the support surface, and the like. Examples of covalent binding include covalent bonds formed between the nucleic acids and a functional group present on the surface of the rigid support (e.g., —OH), where the functional group may be naturally occurring or present as a member of an introduced linking group, as described in greater detail below.

The amount of nucleic acid present in each composition will be sufficient to provide for adequate hybridization and detection of target nucleic acid sequences during the assay in which the array is employed. Generally, the amount of each nucleic acid member stably associated with the support of the array is at least about 0.001 ng, preferably at least about 0.02 ng and more preferably at least about 0.05 ng, where the amount may be as high as 1000 ng or higher, but will usually not exceed about 20 ng. Where the nucleic acid member is "spotted" onto the support in a spot comprising an overall circular dimension, the diameter of the "spot" will generally range from about 10 to 5,000 µm, usually from about 20 to 2,000 µm and more usually from about 100 to 200 µm.

Control nucleic acid members may be present on the array including nucleic acid members comprising oligonucleotides or nucleic acids corresponding to genomic DNA, housekeeping genes, vector sequences, plant nucleic acid sequence, negative and positive control genes, and the like. Control nucleic acid members are calibrating or control genes whose function is not to tell whether a particular "key" gene of interest is expressed, but rather to provide other useful information, such as background or basal level of expression.

Other control nucleic acids are spotted on the array and used as target expression control nucleic acids and mismatch control nucleotides to monitor non-specific binding or cross-hybridization to a nucleic acid in the sample other than the target to which the probe is directed. Mismatch probes thus indicate whether a hybridization is specific or not. For example, if the target is present, the perfectly matched probes should be consistently brighter than the mismatched probes. In addition, if all control mismatches are present, the mismatch probes are used to detect a mutation.

Numerous methods may be used for attachment of the nucleic acid members of the invention to the substrate (a process referred to as "spotting"). For example, nucleic acids are attached using the techniques of, for example U.S. Pat. No. 5,807,522, which is incorporated herein by reference for teaching methods of polymer attachment. Alternatively, spotting may be carried out using contact printing technology as is known in the art.

The measuring of the expression of the RNA product of the invention can be done by using those polynucleotides which are specific and/or selective for the RNA products of the invention to quantitate the expression of the RNA product. In a specific embodiment of the invention, the polynucleotides which are specific and/or selective for the RNA products are probes or primers. In one embodiment, these polynucleotides are in the form of nucleic acid probes which can be spotted onto an array to measure RNA from the sample of an individual to be measured. In another embodiment, commercial arrays can be used to measure the expression of the RNA product. In yet another embodiment, the polynucleotides which are specific and/or selective for the RNA products of the invention are used in the form of probes and primers in techniques such as quantitative real-time RT PCR, using for example SYBR® Green, or using TaqMan® or Molecular Beacon techniques, where the polynucleotides used are used in the form of a forward primer, a reverse primer, a TaqMan labeled probe or a Molecular Beacon labeled probe.

In embodiments where only one or a two genes are to be analyzed, the nucleic acid derived from the sample cell(s) may be preferentially amplified by use of appropriate primers such that only the genes to be analyzed are amplified to reduce background signals from other genes expressed in the breast cell. Alternatively, and where multiple genes are to be analyzed or where very few cells (or one cell) is used, the nucleic acid from the sample may be globally amplified before hybridization to the immobilized polynucleotides. Of course RNA, or the cDNA counterpart thereof may be directly labeled and used, without amplification, by methods known in the art.

4. Use of a Microarray

A "microarray" is a linear or two-dimensional array of preferably discrete regions, each having a defined area, formed on the surface of a solid support such as, but not limited to, glass, plastic, or synthetic membrane. The density of the discrete regions on a microarray is determined by the total numbers of immobilized polynucleotides to be detected on the surface of a single solid phase support, preferably at least about 50/cm$^2$, more preferably at least about 100/cm$^2$, even more preferably at least about 500/cm$^2$, but preferably below about 1,000/cm$^2$. Preferably, the arrays contain less than about 500, about 1000, about 1500, about 2000, about 2500, or about 3000 immobilized polynucleotides in total. As used herein, a DNA microarray is an array of oligonucleotides or polynucleotides placed on a chip or other surfaces used to hybridize to amplified or cloned polynucleotides from a sample. Since the position of each particular group of primers in the array is known, the identities of a sample polynucleotides can be determined based on their binding to a particular position in the microarray.

Determining gene expression levels may be accomplished utilizing microarrays. Generally, the following steps may be involved: (a) obtaining an mRNA sample from a subject and preparing labeled nucleic acids therefrom (the "target nucleic acids" or "targets"); (b) contacting the target nucleic acids with an array under conditions sufficient for the target nucleic acids to bind to the corresponding probes on the array, for example, by hybridization or specific binding; (c) optional removal of unbound targets from the array; (d) detecting the bound targets, and (e) analyzing the results, for example, using computer based analysis methods. As used herein, "nucleic acid probes" or "probes" are nucleic acids attached to the array, whereas "target nucleic acids" are nucleic acids that are hybridized to the array.

A nucleic acid specimen may be obtained from a subject to be tested using either "invasive" or "non-invasive" sampling means. A sampling means is said to be "invasive" if it involves the collection of nucleic acids from within the skin or organs of an animal (including murine, human, ovine, equine, bovine, porcine, canine, or feline animal). Examples of an invasive sampling means include, blood collection, semen collection, needle biopsy, pleural aspiration, umbilical cord biopsy. Examples of such methods are discussed by Kim, et al., *J. Virol.,* 1992, 66:3879-3882, Biswas, et al., *Ann. NY Acad. Sci.,* 1990, 590:582-583, and Biswas, et al., *J. Clin. Microbiol.,* 1991, 29:2228-2233.

In contrast, a "non-invasive" sampling means is one in which the nucleic acid molecules are recovered from an internal or external surface of the animal. Examples of a "non-invasive" sampling means include, "swabbing," collection of tears, saliva, urine, fecal material, or the like.

In one embodiment of the present invention, one or more cells, i.e. a sample, from a subject to be tested are obtained and RNA is isolated from the cells. It is also possible to obtain a cell sample from a subject, and then to enrich the sample for a desired cell type. For example, cells may be isolated from other cells using a variety of techniques, such as isolation with an antibody binding to an epitope on the cell surface of the desired cell type. Where the desired cells are in a solid tissue, particular cells may be dissected, for example, by micro-dissection or by laser capture micro-dissection (LCM) (see, e.g., Bonner, et al., *Science,* 1997, 278:1481, Emmert-Buck, et al., *Science,* 1996, 274:998, Fend, et al., *Am. J. Path.,* 1999, 154:61, and Murakami, et al., *Kidney Hit.,* 2000, 58:1346.

RNA may be extracted from tissue or cell samples by a variety of methods, for example, guanidium thiocyanate lysis followed by CsCl centrifugation (Chirgwin, et al., *Biochemistry,* 1979, 18:5294-5299). RNA from single cells may be obtained as described in methods for preparing cDNA libraries from single cells (see, e.g., Dulac, *Curr. Top. Dev. Biol.,* 1998, 36:245, and Jena, et al., *J. Immunol. Methods,* 1996, 190:199).

The RNA sample can be further enriched for a particular species. In one embodiment, for example, poly(A)+RNA may be isolated from an RNA sample. In another embodiment, the RNA population may be enriched for sequences of interest by primer-specific cDNA synthesis, or multiple rounds of linear amplification based on cDNA synthesis and template-directed in vitro transcription (see, e.g., Wang, et al., *Proc. Natl. Acad. Sci. USA,* 1989, 86:9717; Dulac, et al., supra; Jena, et al., supra). In addition, the population of RNA, enriched or not in particular species or sequences, may be further amplified by a variety of amplification methods including, PCR, ligase chain reaction (LCR) (see, e.g., Wu and Wallace, *Genomics,* 1989, 4:560; Landegren, et al., *Science,* 1988, 241:1077), self-sustained sequence replication (SSR) (see, e.g., Guatelli, et al., *Proc. Natl. Acad. Sci. USA,* 1990, 87:1874), nucleic acid based sequence amplification (NASBA) and transcription amplification (see, e.g., Kwoh, et al., *Proc. Natl. Acad. Sci. USA,* 1989, 86:1173). Methods for PCR technology are well known in the art (see, e.g., *PCR Technology: Principles and Applications for DNA Amplification,* ed. H. A. Erlich, Freeman Press, N.Y., N.Y., 1992; *PCR Protocols: A Guide to Methods and Applications,* eds. Innis, et al., Academic Press, San Diego, Calif., 1990; Mattila, et al., *Nucleic Acids Res.,* 1991, 19:4967; Eckert, et al., *PCR Methods and Applications*, 1991, 1:17; PCR, eds. McPherson et al., IRL Press, Oxford; and U.S. Pat. No. 4,683,202). Methods of amplification are described, for example, by Ohyama, et al., *BioTechniques*, 2000, 29:530; Luo, et al., *Nat. Med.*, 1999, 5:117; Hegde, et al., *BioTechniques*, 2000, 29:548; Kacharmina, et al., *Meth. Enzymol.*, 1999, 303:3; Livesey, et al., *Curr. Biol.*, 2000, 10:301; Spirin, et al., *Invest. Ophtalmol. Vis. Sci.*, 1999, 40:3108; and Sakai, et al., *Anal. Biochem.*, 2000, 287:32. RNA amplification and cDNA synthesis may also be conducted in cells in situ (see, e.g., Eberwine, et al., *Proc. Natl. Acad. Sci. USA*, 1992, 89:3010).

In yet another embodiment of the invention, all or part of a disclosed marker sequence may be amplified and detected by methods such as the polymerase chain reaction (PCR) and variations thereof, such as, but not limited to, quantitative PCR (Q-PCR), reverse transcription PCR (RT-PCR), and real-time PCR, optionally real-time RT-PCR. Such methods would utilize one or two primers that are complementary to portions of a disclosed sequence, where the primers are used to prime nucleic acid synthesis.

The newly synthesized nucleic acids are optionally labeled and may be detected directly or by hybridization to a polynucleotide of the invention.

The nucleic acid molecules may be labeled to permit detection of hybridization of the nucleic acid molecules to a microarray. That is, the probe may comprise a member of a signal producing system and thus, is detectable, either directly or through combined action with one or more additional members of a signal producing system. For example, the nucleic acids may be labeled with a fluorescently labeled dNTP (see, e.g., Kricka, *Nonisotopic DNA Probe Techniques*, Academic Press San Diego, Calif., 1992), biotinylated dNTPs or rNTP followed by addition of labeled streptavidin, chemiluminescent labels, or isotopes. Another example of labels includes "molecular beacons" as described in Tyagi and Kramer, *Nature Biotech.*, 1996, 14:303. The newly synthesized nucleic acids may be contacted with polynucleotides (containing sequences) of the invention under conditions which allow for their hybridization. Hybridization may be also determined, for example, by plasmon resonance (see, e.g., Thiel, et al., *Anal. Chem.*, 1997, 69:4948).

In one embodiment, a plurality, for example, two sets of target nucleic acids are labeled and used in one hybridization reaction ("multiplex" analysis). One set of nucleic acids may correspond to RNA from one cell and another set of nucleic acids may correspond to RNA from another cell. The plurality of sets of nucleic acids may be labeled with different labels, such as different fluorescent labels (e.g., fluorescein and rhodamine), which have distinct emission spectra so that they can be distinguished. The sets may then be mixed and hybridized simultaneously to one microarray (see, e.g., Shena, et al., *Science*, 1995, 270:467-470).

A number of different microarray configurations and methods for their production are known to those of skill in the art and are disclosed in U.S. Pat. Nos. 5,242,974; 5,384,261; 5,405,783; 5,412,087; 5,424,186; 5,429,807; 5,436,327; 5,445,934; 5,556,752; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,624,711; 5,700,637; 5,744,305; 5,770, 456; 5,770,722; 5,837,832; 5,856,101; 5,874,219; 5,885,837; 5,919,523; 6,022,963; 6,077,674; and 6,156,501; Shena, et al., Tibtech 16:301, 1998; Duggan, et al., Nat. Genet. 21:10, 1999; Bowtell, et al., Nat. Genet. 21:25, 1999; Lipshutz, et al., 21 Nature Genet. 20-24, 1999; Blanchard, et al., 11 Biosensors and Bioelectronics, 687-90, 1996; Maskos, et al., 21 Nucleic Acids Res. 4663-69, 1993; Hughes, et al., Nat. Biotechol. (2001) 19:342; the disclosures of which are herein incorporated by reference. Patents describing methods of using arrays in various applications include: U.S. Pat. Nos. 5,143,854; 5,288,644; 5,324,633; 5,432,049; 5,470, 710; 5,492,806; 5,503,980; 5,510,270; 5, 525,464; 5,547, 839; 5,580,732; 5,661,028; 5,848,659; and 5,874,219; the disclosures of which are herein incorporated by reference.

In one embodiment, an array of oligonucleotides may be synthesized on a solid support. Exemplary solid supports include glass, plastics, polymers, metals, metalloids, ceramics, organics, etc. Using chip masking technologies and photoprotective chemistry, it is possible to generate ordered arrays of nucleic acid probes. These arrays, which are known, for example, as "DNA chips" or very large scale immobilized polymer arrays ("VLSIPS®" arrays), may include millions of defined probe regions on a substrate having an area of about 1 $cm^2$ to several $cm^2$, thereby incorporating from a few to millions of probes (see, e.g., U.S. Pat. No. 5,631,734).

To compare expression levels, labeled nucleic acids may be contacted with the array under conditions sufficient for binding between the target nucleic acid and the probe on the array. In one embodiment, the hybridization conditions may be selected to provide for the desired level of hybridization specificity; that is, conditions sufficient for hybridization to occur between the labeled nucleic acids and probes on the microarray.

Hybridization may be carried out in conditions permitting essentially specific hybridization. The length and GC content of the nucleic acid will determine the thermal melting point and thus, the hybridization conditions necessary for obtaining specific hybridization of the probe to the target nucleic acid. These factors are well known to a person of skill in the art, and may also be tested in assays. An extensive guide to nucleic acid hybridization may be found in Tijssen, et al., *Laboratory Techniques in Biochemistry and Molecular Biology, Vol. 24: Hybridization with Nucleic Acid Probes*, P. Tijssen, ed. Elsevier, N. Y., 1993.

The methods described above will result in the production of hybridization patterns of labeled target nucleic acids on the array surface. The resultant hybridization patterns of labeled nucleic acids may be visualized or detected in a variety of ways, with the particular manner of detection selected based on the particular label of the target nucleic acid. Representative detection means include scintillation counting, autoradiography, fluorescence measurement, calorimetric measurement, light emission measurement, light scattering, and the like.

One such method of detection utilizes an array scanner that is commercially available (Affymetrix, Santa Clara, Calif.), for example, the 417® Arrayer, the 418® Array Scanner, or the Agilent GeneArray® Scanner. This scanner is controlled from a system computer with an interface and easy-to-use software tools. The output may be directly imported into or directly read by a variety of software applications. Exemplary scanning devices are described in, for example, U.S. Pat. Nos. 5,143,854 and 5,424,186.

Dosing and Routes of Administration

With regard to the WEE1 inhibitors of the invention, various preparation forms can be selected, and examples thereof include oral preparations such as tablets, capsules, powders, granules or liquids, or sterilized liquid parenteral preparations such as solutions or suspensions, suppositories, ointments and the like. The WEE1 inhibitors are available as pharmaceutically acceptable salts. The WEE1 inhibitors of the invention are prepared with pharmaceutically acceptable carriers or diluents.

The term "pharmaceutically acceptable salt" as referred to in this description means ordinary, pharmaceutically acceptable salt. For example, when the compound has a hydroxyl group, or an acidic group such as a carboxyl group and a tetrazolyl group, then it may form a base-addition salt at the hydroxyl group or the acidic group; or when the compound has an amino group or a basic heterocyclic group, then it may form an acid-addition salt at the amino group or the basic heterocyclic group.

The base-addition salts include, for example, alkali metal salts such as sodium salts, potassium salts; alkaline earth metal salts such as calcium salts, magnesium salts; ammonium salts; and organic amine salts such as trimethylamine salts, triethylamine salts, dicyclohexylamine salts, ethanolamine salts, diethanolamine salts, triethanolamine salts, procaine salts, N,N'-dibenzylethylenediamine salts.

The acid-addition salts include, for example, inorganic acid salts such as hydrochlorides, sulfates, nitrates, phosphates, perchlorates; organic acid salts such as maleates, fumarates, tartrates, citrates, ascorbates, trifluoroacetates; and sulfonates such as methanesulfonates, isethionates, benzenesulfonates, p-toluenesulfonates.

The term "pharmaceutically acceptable carrier or diluent" refers to excipients, (e.g., fats, beeswax, semi-solid and liquid polyols, natural or hydrogenated oils, etc.], water (e.g., distilled water, particularly distilled water for injection, etc.), physiological saline, alcohol (e.g., ethanol), glycerol, polyols, aqueous glucose solution, mannitol, plant oils, etc.), and additives (e.g., extending agent, disintegrating agent, binder, lubricant, wetting agent, stabilizer, emulsifier, dispersant, preservative, sweetener, colorant, seasoning agent or aromatizer, concentrating agent, diluent, buffer substance, solvent or solubilizing agent, chemical for achieving storage effect, salt for modifying osmotic pressure, coating agent or antioxidant, and the like).

Solid preparations can be prepared in the forms of tablet, capsule, granule and powder without any additives, or prepared using appropriate carriers (additives). Examples of such carriers (additives) may include saccharides such as lactose or glucose; starch of corn, wheat or rice; fatty acids such as stearic acid; inorganic salts such as magnesium metasilicate aluminate or anhydrous calcium phosphate; synthetic polymers such as polyvinylpyrrolidone or polyalkylene glycol; alcohols such as stearyl alcohol or benzyl alcohol; synthetic cellulose derivatives such as methylcellulose, carboxymethylcellulose, ethylcellulose or hydroxypropylmethylcellulose; and other conventionally used additives such as gelatin, talc, plant oil and gum arabic.

These solid preparations such as tablets, capsules, granules and powders may generally contain, for example, 0.1 to 100% by weight, and preferably 5 to 98% by weight, of the WEE1 inhibitor, based on the total weight of each preparation.

Liquid preparations are produced in the forms of suspension, syrup, injection and drip infusion (intravenous fluid) using appropriate additives that are conventionally used in liquid preparations, such as water, alcohol or a plant-derived oil such as soybean oil, peanut oil and sesame oil.

In particular, when the preparation is administered parenterally in a form of intramuscular injection, intravenous injection or subcutaneous injection, appropriate solvent or diluent may be exemplified by distilled water for injection, an aqueous solution of lidocaine hydrochloride (for intramuscular injection), physiological saline, aqueous glucose solution, ethanol, polyethylene glycol, propylene glycol, liquid for intravenous injection (e.g., an aqueous solution of citric acid, sodium citrate and the like) or an electrolytic solution (for intravenous drip infusion and intravenous injection), or a mixed solution thereof.

Such injection may be in a form of a preliminarily dissolved solution, or in a form of powder per se or powder associated with a suitable carrier (additive) which is dissolved at the time of use. The injection liquid may contain, for example, 0.1 to 10% by weight of an active ingredient based on the total weight of each preparation.

Liquid preparations such as suspension or syrup for oral administration may contain, for example, 0.1 to 10% by weight of an active ingredient based on the total weight of each preparation.

Each preparation in the invention can be prepared by a person having ordinary skill in the art according to conventional methods or common techniques. For example, a preparation can be carried out, if the preparation is an oral preparation, for example, by mixing an appropriate amount of the compound of the invention with an appropriate amount of lactose and filling this mixture into hard gelatin capsules which are suitable for oral administration. On the other hand, preparation can be carried out, if the preparation containing the compound of the invention is an injection, for example, by mixing an appropriate amount of the compound of the invention with an appropriate amount of 0.9% physiological saline and filling this mixture in vials for injection.

The components of this invention may be administered to mammals, including humans, either alone or, in combination with pharmaceutically acceptable carriers, excipients or diluents, in a pharmaceutical composition, according to standard pharmaceutical practice. The components can be administered orally or parenterally, including the intravenous, intramuscular, intraperitoneal, subcutaneous, rectal and topical routes of administration.

Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved. Further information about suitable dosages is provided below.

The term "administration" and variants thereof (e.g., "administering" a compound) in reference to a component of the invention means introducing the component or a prodrug of the component into the system of the animal in need of treatment. When a component of the invention or prodrug thereof is provided in combination with one or more other active agents (e.g., the WEE1 inhibitor), "administration" and its variants are each understood to include concurrent and sequential introduction of the component or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits a biological or medicinal response in a tissue, system, animal or human, that is being sought by a researcher, veterinarian, medical doctor or other clinician.

This includes combination therapy involving the use of multiple therapeutic agents, such as a combined amount of a first and second treatment where the combined amount will achieve the desired biological response. The desired biological response is partial or total inhibition, delay or prevention of the progression of cancer including cancer metastasis; inhibition, delay or prevention of the recurrence of cancer including cancer metastasis; or the prevention of the onset or development of cancer (chemoprevention) in a mammal, for example a human.

A suitable amount of a WEE1 inhibitor is administered to a patient undergoing treatment for cancer. In an embodiment, a WEE1 inhibitor is administered in doses ranging from about 100 mg per day to 250 mg per day. In an embodiment of the invention, a WEE1 inhibitor is administered twice daily (BID), over the course of two and a half days, for a total of 5 doses. In another embodiment of the invention, a WEE1 inhibitor is administered once daily (QD) over the course of two days, for a total of 2 doses.

In an embodiment of the invention, a WEE1 inhibitor can be administered 5 times per week. In another embodiment of the invention, a WEE1 inhibitor can be administered 2 times per week.

Indications

In one embodiment, the invention herein is a method of treating a patient diagnosed with a WEE1 associated cancer with a WEE1 inhibitor, wherein said patient is characterized as having low expression of PKMYT1. The WEE1 inhibitor of the invention has a kinase-inhibitory effect, especially a WEE1 kinase-inhibitory effect, and, as such, it is therefore useful as a remedy for various cancers associated with WEE1 kinase. Examples of a WEE1 kinase associated cancer include, but are not limited to, brain cancer, cervicocerebral cancer, esophageal cancer, thyroid cancer, small cell cancer, non-small cell cancer, breast cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' cancer, skin cancer, malignant melanoma, neuroblastoma, osteosarcoma, Ewing's tumor, soft part sarcoma, acute leukemia, chronic lymphatic leukemia, chronic myelocytic leukemia, Hodgkin's lymphoma, or as sensitizers for chemo therapy or radiation therapy of those cancers.

In particular, the WEE1 inhibitor of the invention are useful as remedies, for example, for breast cancer, lung cancer, pancreatic cancer, colon cancer, ovarian cancer, acute leukemia, chronic lymphatic leukemia, chronic myelocytic leukemia, Hodgkin's lymphoma, or as sensitizers for chemotherapy or radiation therapy of those cancers.

In addition to the treatment of the WEE1 kinase associated cancers above, the WEE1 inhibitor may also be useful for the treatment of the following cancers: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; and Skin: malignant melanoma, basal cell carcinoma, squamous cell carcinoma, Karposi's sarcoma, moles dysplastic nevi, lipoma, angioma, dermatofibroma. Thus, the term "cancerous cell" as provided herein, includes a cell afflicted by any one of the above-identified conditions.

Further included within the scope of the invention is a method of treating or preventing a disease in which angiogenesis is implicated, which is comprised of administering to a mammal in need of such treatment a therapeutically effective amount of the combination of the present invention. Ocular neovascular diseases are an example of conditions where much of the resulting tissue damage can be attributed to aberrant infiltration of blood vessels in the eye (WO 2000/30651). The undesirable infiltration can be triggered by ischemic retinopathy, such as that resulting from diabetic retinopathy, retinopathy of prematurity, retinal vein occlusions, etc., or by degenerative diseases, such as the choroidal neovascularization observed in age-related macular degeneration Inhibiting the growth of blood vessels by administration of the present compounds would therefore prevent the infiltration of blood vessels and prevent or treat diseases where angiogenesis is implicated, such as ocular diseases like retinal vascularization, diabetic retinopathy, age-related macular degeneration, and the like.

Further included within the scope of the invention is a method of treating or preventing a non-malignant disease in which angiogenesis is implicated, including but not limited to: ocular diseases (such as, retinal vascularization, diabetic retinopathy and age-related macular degeneration), atherosclerosis, arthritis, psoriasis, obesity and Alzheimer's disease (Dredge, et al., *Expert Opin. Biol. Ther.,* 2002, 2(8): 953-966). In another embodiment, a method of treating or preventing a disease in which angiogenesis is implicated includes: ocular diseases (such as, retinal vascularization, diabetic retinopathy and age-related macular degeneration), atherosclerosis, arthritis and psoriasis.

Further included within the scope of the invention is a method of treating hyperproliferative disorders, such as, restenosis, inflammation, autoimmune diseases, and allergy/asthma.

Further included within the scope of the invention is the use of the instant combination to coat stents and, therefore, the use of the instant compounds on coated stents for the treatment and/or prevention of restenosis (WO 2003/032809).

Further included within the scope of the invention is the use of the instant combination for the treatment and/or prevention of osteoarthritis (WO 2003/035048).

Further included within the scope of the invention is a method of treating hypoinsulinism.

Exemplifying the invention is the use of the WEE1 inhibitor described above in the preparation of a medicament for the treatment of a WEE1 associated cancer.

Additional Anti-Cancer Agents

The WEE1 inhibitor administered in the methods of the instant invention is also useful in combination with additional therapeutic, chemotherapeutic and anti-cancer agents. Further combination with a WEE1 inhibitor of the instant invention with therapeutic, chemotherapeutic and anti-cancer agents are within the scope of the invention. Examples of such agents can be found in *Cancer Principles and Practice of Oncology* by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such additional agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The mTOR inhibitor and αvβ3 integrin antagonist combination of the instant invention may be particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators inclue finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors, such as ridaforolimus, everolimus, temsirolimus, sirolimus or a rapamycin-analog.

An example of a hypoxia activated compound is tirapazamine.

Examples of proteosome inhibitors include but are not limited to lactacystin and MLN-341 (Velcade).

Examples of microtubule inhibitors/microtubule-stabilizing agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR 109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butyl-amide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H)

propanamine, 1-amino-9-ethyl-5-fluoro-2,3-dihydro-9-hydroxy-4-methyl-1H,12H-benzo [de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB, 8aa,9b)-9-[2-[N-[2-(dimethylamino)ethyl]-N-methylamino]ethyl]-5-[4-hydro0xy-3,5-dimethoxyphenyl]-5,5a,6,8,8a,9-hexohydrofuro(3',4':6,7) naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo [4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c] quinolin-7-one, and dimesna.

Examples of inhibitors of mitotic kinesins, and in particular the human mitotic kinesin KSP, are described in Publications WO 2003/039460, WO 2003/050064, WO 2003/050122, WO 2003/049527, WO 2003/049679, WO 2003/049678, WO 2004/039774, WO 2003/079973, WO 2003/099211, WO 2003/105855, WO 2003/106417, WO 2004/037171, WO 2004/058148, WO 2004/058700, WO 2004/126699, WO 2005/018638, WO 2005/019206, WO 2005/019205, WO 2005/018547, WO 2005/017190, US 2005/0176776. In an embodiment inhibitors of mitotic kinesins include, but are not limited to, inhibitors of KSP, inhibitors of MKLP1, inhibitors of CENP-E, inhibitors of MCAK, and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A., et al., *J. Med. Chem.*, 2003, 46(24):5097-5116.

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone, and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include, but are not limited to, lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896), atorvastatin (LIPITOR®; see U.S. Pat. Nos. 5,273, 995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, Cholesterol Lowering Drugs, *Chemistry & Industry*, 1996, pp. 85-89, and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. Nos. 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis, see, *European J. of Cancer*, 1999, 35(9):1394-1401.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs), like aspirin and ibuprofen, as well as selective cyclooxy-genase-2 inhibitors like celecoxib and rofecoxib (*PNAS*, 1992, 89:7384; *JNCI*, 1982, 69:475; *Arch. Opthalmol.*, 1990, 108:573; *Anat. Rec.*, 1994, 238:68; *FEBS Letters*, 1995, 372:83; *Clin, Orthop.*, 1995, 313:76; *J. Mol. Endocrinol.*, 1996, 16:07; *Jpn. J. Pharmacol.*, 1997, 75:105; *Cancer Res.*, 1997, 57:1625; *Cell*, 1998, 93:705; *Intl. J. Mol. Med.*, 1998, 2:715; *J. Biol. Chem.*, 1999. 274:9116), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see, Fernandez, et al., *J. Lab. Clin. Med.*, 1985, 105:141-145), and antibodies to VEGF (see, Nature Biotechnology, 1999, 17:963-968); Kim, et al., *Nature*, 1993, 362:841-844; WO 2000/44777; and WO 2000/61186).

Other therapeutic agents that modulate or inhibit angiogenesis and may also be used in combination with the compounds of the instant invention, include agents that modulate or inhibit the coagulation and fibrinolysis systems (see, review in *Clin. Chem. La. Med.*, 2000, 38:679-692). Examples of such agents that modulate or inhibit the coagulation and fibrinolysis pathways include, but are not limited to, heparin (see, *Thromb. Haemost.*, 1998, 80:10-23), low molecular weight heparins and carboxypeptidase U inhibitors (also known as, inhibitors of active thrombin activatable fibrinolysis inhibitor [TAFIa]) (see, *Thrombosis Res.*, 2001, 101:329-354). TAFIa inhibitors have been described in PCT International Publication WO 2003/013526. "Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, and CHK1 kinases and cdk and cdc kinase inhibitors and are specifically exemplified by 7-hydroxy-staurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature*, 2001, 411:355-365.

"Inhibitors of cell proliferation and survival signaling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, WO 2006/135627, WO 2006/091395, WO 2006/110638), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

Specific anti-IGF-1R antibodies include, but are not limited to, dalotuzumab, figitumumab, cixutumumab, SHC 717454, Roche R1507, EM164 or Amgen AMG479.

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 μM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to, those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344, 991, 5,134,142, 5,380,738, 5,393,790, 5,466,823, 5,633,272, and 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine, or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_{v\beta3}$ integrin, to compounds which selectively antagonize, inhibit or counteract binding of a physiological ligand to the αvβ5 integrin, to compounds which antagonize, inhibit or counteract binding of a physiological ligand to both the $\alpha_{v\beta3}$ integrin and the $\alpha_{v}\beta_{5}$ integrin, and to compounds which antagonize, inhibit or counteract the activity of the particular integrin(s) expressed on capillary endothelial cells. The term also refers to antagonists of the $\alpha_{v}\beta_{6}$, $\alpha_{v}\beta_{8}$, $\alpha_{1}\beta_{1}$, $\alpha_{2}\beta_{1}$, $\alpha_{1}\beta_{1}$, $\alpha_{6}\beta_{1}$, and $\alpha_{6}\beta_{4}$ integrins. The term also refers to antagonists of any combination of $\alpha_{v}\beta_{3}$, $\alpha_{v}\beta_{5}$, $\square\alpha_{v}\beta_{6}$, $\alpha_{v}\beta_{8}$, $\alpha_{1}\beta_{1}$, $\alpha_{2}\beta_{1}$, $\alpha_{5}\beta_{1}$, $\alpha_{6}\beta_{1}$, and $\alpha_{6}\beta_{4}$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3, 9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the mTOR inhibitor and αvβ3 integrin antagonist combination of the instant invention with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see, *J. Cardiovasc. Pharmacol.*, 1998, 31:909-913; *J. Biol. Chem.*, 1999, 274:9116-9121; *Invest. Ophthalmol Vis. Sci.*, 2000, 41:2309-2317). More recently, PPAR-γ agonists have been shown to inhibit the angiogenic response to VEGF in vitro; both troglitazone and rosiglitazone maleate inhibit the development of retinal neovascularization in mice (*Arch. Ophthamol.*, 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treat cancer, see, Hall, et al., *Am. J. Hum. Genet.*, 1997, 61:785-789 and Kufe, et al., *Cancer Medicine*, 5th Ed, B. C. Decker, Hamilton, 2000, pp 876-889. Gene therapy can be used to deliver any tumor suppressing gene. Examples of such genes include, but are not limited to, p53, which can be delivered via recombinant virus-mediated gene transfer (see, U.S. Pat. No. 6,069,134), a uPA/uPAR antagonist (*Gene Therapy*, 1998, 5(8):1105-13), and interferon gamma (*J. Immunol.*, 2000, 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as, the phenothiazines (for example, prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

The WEE1 inhibitor of the instant invention may also be administered with an agent useful in the treatment of anemia. Such an anemia treatment agent is, for example, a continuous erythropoiesis receptor activator (such as, Epoetin alfa).

The WEE1 inhibitor of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

The WEE1 inhibitor of the instant invention may also be administered with an immunologic-enhancing drug, such as levamisole, isoprinosine and Zadaxin.

The WEE1 inhibitor of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

The WEE1 inhibitor of the instant invention may also be useful for treating or preventing breast cancer in combination with aromatase inhibitors.

Examples of aromatase inhibitors include but are not limited to: anastrozole, letrozole and exemestane.

The WEE1 inhibitor of the instant invention may also be useful for treating or preventing cancer in combination with siRNA therapeutics.

The WEE1 inhibitor of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

The WEE1 inhibitor of the instant invention may also be useful for treating or preventing cancer in combination with inhibitors of Akt. Such inhibitors include compounds described in, but not limited to, the following publications: WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, WO 2006/135627, WO 2006091395, WO 2006/110638).

The WEE1 inhibitor of the instant invention may also be useful for treating or preventing cancer in combination with PARP inhibitors.

Radiation therapy itself means an ordinary method in the field of treatment of cancer. For radiation therapy, employable are various radiations such as X-ray, γ-ray, neutron ray, electron beam, proton beam; and radiation sources. In a most popular radiation therapy, a linear accelerator is used for irradiation with external radiations, γ-ray.

The WEE1 inhibitor of the instant invention may also be useful for treating cancer in further combination with the following therapeutic agents: abarelix (Plenaxis Depot®); abiraterone acetate (Zytiga®); (Actiq®); aldesleukin (Prokine®); Aldesleukin (Proleukin®); Alemtuzumab (Campath®); alfuzosin HCl (UroXatral®); alitretinoin (Panretin®); allopurinol (Zyloprim®); altretamine (Hexalen®); amifostine (Ethyol®); anastrozole (Arimidex®); (Anzemet®); (Anexsia®); aprepitant (Emend®); arsenic trioxide (Trisenox®); asparaginase (Elspar®); azacitidine (Vidaza®); bendamustine hydrochloride (Treanda®); bevacuzimab (Avastin®); bexarotene capsules (Targretin®); bexarotene gel (Targretin®); bleomycin (Blenoxane®); bortezomib (Velcade®); (Brofenac®); busulfan intravenous (Busulflex®); busulfan oral (Myleran®); cabazitaxel (Jevtana®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cinacalcet (Sensipar®); cisplatin (Platino®); cladribine (Leustatin®, 2-CdA®); clofarabine (Clolar®); cyclophosphamide (Cytoxan®, Neosa®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); dasatinib (Sprycel®); daunorubicin liposomal (DanuoXome®); daunorubicin, daunomycin (Daunorubicin®); daunorubicin, daunomycin (Cerubidine®); decitabine (Dacogen®); degarelix (Degarelix®); Denileukin diftitox (Ontak®); denosumab (Xgeva®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); eribulin mesylate (Halaven®); erlotinib (Tarceva®); estramustine (Emcyt®); etoposide phosphate (Etopophos®); etoposide, VP-16 (Vepesid®); everolimus (Afinitor®); exemestane (Aromasin®); fentanyl buccal (Onsolis®); fentanyl citrate (Fentora®); fentanyl sublingual tablets (Abstral®); Filgrastim (Neupogen®); floxuridine (intraarterial) (FUDR®); fludarabine (Fludara®); fluorouracil, 5-FU (Adrucil®); flutamide (Eulexin®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); granisetron (Kytril Solution®) (Sancuso®); histrelin acetate (Histrelin Implant®); human papillomavirus bivalent vaccine (Cervarix®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); ipilimumab (Yervoy®); irinotecan (Camptosar®); (Kadian®); ixabepilone (Ixempra®); lapatinib (Tykerb®); lenalidomide (Revlimid®); letrozole (Femara®); leucovorin (Wellcovorin®, Leucovorin®); Leuprolide Acetate (Eligard®); (Lupron Depot®); (Viadur®); levamisole (Ergamisol®); levoleucovorin (Fusilev®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitomycin C (Mitozytrex®); mitotane (Lysodren®); mitoxantrone (Novantrone®); nandrolone phenpropionate (Durabolin-50®); nelarabine (Arranon®); nilotinib hydrochloride monohydrate (Tasigna®); Nofetumomab (Verluma®); ofatumumab (Arzerra®); ondansetron (Zuplenz®); Oprelvekin (Neumega®); (Neupogen®); oxaliplatin (Eloxatin®); paclitaxel (Paxene®); paclitaxel (Taxol®); paclitaxel protein-bound particles (Abraxane®); palifermin (Kepivance®); palonosetron (Aloxi®); pamidronate (Aredia®); panitumumab (Vectibix®); pazopanib (Votrient®); pegademase (Adagen (Pegademase Bovine)®); pegaspargase (Oncaspar®); Pegfilgrastim (Neulasta®); peginterferon alfa-2B (Sylatron®); pemetrexed disodium (Alimta®); pentostatin (Nipent®); pipobroman (Vercyte®); plerixafor injection (Mozobil®); plicamycin, mithramycin (Mithracin®); porfimer sodium (Photofrin®); pralatrexate injection (Folotyn®); procarbazine (Matulane®); (Quadramet®); quadrivalent human papillomavirus (types 6, 11, 16, 18) recombinant vaccine (Gardasil®); quinacrine (Atabrine®); raloxifene hydrochloride (Evista®); Rasburicase (Elitek®); Rituximab (Rituxan®); romidepsin (Istodax®); sargramostim (Leukine®); Sargramostim (Prokine®); secretin (SecreFlo®); sipuleucel-T (Provenge®); sorafenib (Nexavar®); streptozocin (Zanosar®); sunitinib maleate (Sutent®); talc (Sclerosol®); tamoxifen (Nolvadex®); temozolomide (Temodar®); temsirolimus (Torisel®); teniposide, VM-26 (Vumon®); (Temodar®); testolactone (Teslac®); thalidomide (Thalomid®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); (Trelstar LA®); tretinoin, ATRA (Vesanoid®); triptorelin pamoate (Trelstar Depot®); (UltraJect®); Uracil Mustard (Uracil Mustard Capsules®); valrubicin (Valstar®); vandetanib (Vandetanib®); vinblastine (Velban®); vincristine (Oncovin®); vinorelbine (Navelbine®); vorinostat (Zolinza®); (Zofran ODT®); and zoledronate (Zometa®).

All patents, publications and pending patent applications identified are hereby incorporated by reference.

EXAMPLES

Example 1

Preparation of WEE1-1

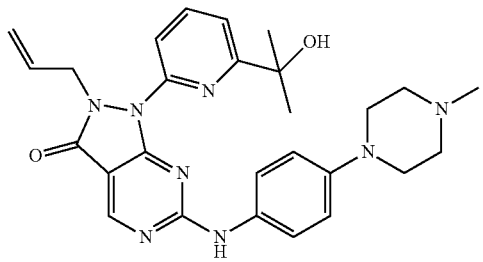 [SMILES: C=CCn1c(=O)c2cnc(Nc3ccc(N4CCN(C)CC4)cc3)nc2n1-c1cccc(C(C)(C)O)n1]

Production of 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one Step 1) Production of 2-(6-bromo-2-pyridinyl)-2-propanol In a nitrogen atmosphere, 30 mL of 3 M methylmagnesium iodide/diethyl ether was added to 300 mL of diethyl ether solution of 8.72 g of methyl 6-bromopyridine-2-carboxylate. Water and 2 N hydrochloric acid were added to the reaction liquid, and extracted with ethyl acetate. This was washed with aqueous saturated sodium hydrogencarbonate solution and saturated saline water, and dried with anhydrous magnesium sulfate. The solvent was evaporated away under reduced pressure to obtain crude 2-(6-bromo-2-pyridinyl)-2-propanol as a yellow oily substance. $^1$H-NMR (400 MHz, CDCl3) δ: 7.56 (1H, t, J=7.8 Hz), 7.38 (1H, dd, J=7.8, 1.0 Hz), 7.36 (1H, dd, J=7.8, 1.0 Hz), 1.55 (6H, s). ESI-MS Found: m/z[M+H]+ 216, 218.

Step 2) Production of 2-allyl-1-[6-(1-hydroxy-1-methylethyl)-2-pyridinyl]-6-(methylthio)-1,2-dihydro-3H-pyrazolo[3,4-d]pyrimidin-3-one The entitled compound was obtained in the same manner as in Preparative Example 1-1, for which, however, the compound obtained in the above reaction was used in place of 2-iodopyridine used in Preparative Example 1-1. $^1$H-NMR (400 MHz, CDCl$_3$) δ: 8.95 (1H, s), 7.91 (1H, t, J=8.0 Hz), 7.76 (1H, d, J=7.3 Hz), 7.40 (1H, dd, J=7.8, 1.0 Hz), 5.70 (1H, ddt, J=17.1, 10.2, 6.3 Hz), 5.06 (1H, dd, J=10.2, 1.0 Hz), 4.93 (1H, dd, J=17.1, 1.2 Hz), 4.81 (2H, d, J=6.3 Hz), 2.59 (4H, s), 1.59 (6H, s). ESI-MS Found: m/z[M+H]+:358.

Step 3) Production of 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one 817 mg of m-chloroperbenzoic acid (>65%) was added to toluene (20 mL) solution of 1.10 g of the above produce, and stirred for 20 minutes. 1.61 mL of N,N-diisopropylethylamine and 706 mg of 4-(4-methylpiperazin-1-yl)aniline were added to the reaction liquid, and stirred overnight. Aqueous saturated sodium hydrogencarbonate solution was added to the reaction liquid, extracted with ethyl acetate, washed with saturated saline water, and dried with anhydrous magnesium sulfate. The solvent was evaporated away, and the residue was purified through basic silica gel column chromatography (hexane/ethyl acetate=1/1 to 0/1, ethyl acetate/ethanol=98/2). After concentrated, this was recrystallized from ethyl acetate to obtain the entitled compound as a yellow solid. $^1$H-NMR (400 MHz, CDCl$_3$) δ: 8.83 (1H, s), 7.86 (1H, dd, J=8.0, 7.8 Hz), 7.75 (1H, d, J=7.3 Hz), 7.49 (1H, brs), 7.48 (2H, d, J=9.0 Hz), 7.34 (1H, d, J=7.4 Hz), 6.93 (2H, d, J=9.0 Hz), 5.70 (1H, ddt, J=17.2, 10.0, 6.5 Hz), 5.04 (1H, d, J=10.0 Hz), 4.94 (1H, d, J=17.2 Hz), 4.74 (2H, d, J=6.5 Hz), 3.26 (4H, t, J=4.8 Hz), 2.73 (4H, brs), 2.44 (3H, s), 1.59 (6H, s). ESI-MS Found: m/z[M+H]+ 501.

Preparative Example 1-1

Production of 2-allyl-6-(methylthio)-1-pyridin-2-yl-3H-pyrazolo[3,4-d]pyrimidin-3-one 2.4 mL of N,N'-dimethylethylenediamine was added to 1,4-dioxane (50 mL) solution of 4.44 g of 2-allyl-6-(methylthio)-1,2-dihydro-3H-pyrazolo[3,4-d]pyrimidin-3-one, 3.80 g of copper(I) iodide, 5.33 g of 2-iodopyridine and 3.80 g of potassium carbonate, and stirred overnight at 95° C. The reaction liquid was cooled, aqueous ammonia was added thereto and extracted with ethyl acetate, washed with saturated saline water and dried with anhydrous magnesium sulfate. The solvent was evaporated away under reduced pressure, and crystallized with ethyl acetate to obtain the entitled compound as a white solid. $^1$H-NMR (400 MHz, CDCl$_3$) δ: 8.94 (1H, s), 8.52 (1H, d, J=5.1 Hz), 7.90 (2H, d, J=3.5 Hz), 7.29-7.25 (1H, m), 5.68 (1H, ddt, J=17.0, 10.2, 6.3 Hz), 5.05 (1H, d, J=10.2 Hz), 4.91 (1H, d, J=17.0 Hz), 4.85 (1H, d, J=6.3 Hz), 2.58 (3H, s).

Example 2

Preparation of WEE1-2

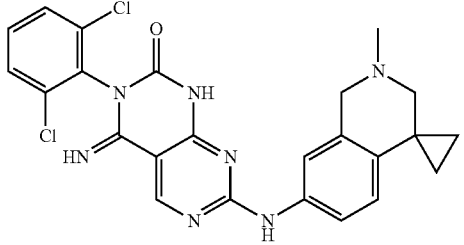 [SMILES: CN1Cc2cc(Nc3ncc4c(=N)n(-c5c(Cl)cccc5Cl)c(=O)[nH]c4n3)ccc2C2(CC2)C1]

Production of 3-(2,6-dichlorophenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one A 1-butanol solution of 1.5 g of 7-chloro-3-(2,6-dichlorophenyl)-4-imino-3,4-dihydropyrimido[4,5-d]pyrimidin-2(1H)-one obtained in Preparative Example 2-1, 1 g of 2'-methyl-2',3'-dihydro-1'H-spiro[cyclopropane-1,4'-isoquinolin]-7'-amine obtained in Preparative Example 2-2, and 0.83 g of p-toluene sulfonic acid monohydrate was stirred at 90° C. for 15 minutes. The reaction liquid was cooled, diluted with chloroform, and the organic layer was washed with aqueous saturated sodium bicarbonate solution and then saturated saline water, and dried with anhydrous magnesium sulfate, filtered, and the solvent was evaporated away. Thus obtained, the roughly-purified product was purified through basic silica gel column chromatography to obtain 3-(2,6-dichlorophenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one. This was dissolved in a mixed solvent of chloroform/methanol, and 1.5 equivalents of aqueous hydrochloric acid solution was added thereto, and stirred at room temperature for 5 minutes. Then, the solvent was evaporated away, and the residue was washed with ethyl acetate to obtain 3-(2,6-dichlorophenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one dihydrochloride as a yellow solid. $^1$H-NMR (400 MHz, DMSO-d$_6$) δ: 11.83 (1H, brs), 10.05 (1H, brs), 9.10 (1H, s), 8.88 (1H, s), 7.79-7.68 (1H, m), 7.63-7.59 (2H, m), 7.47 (1H, t, J=8.2 Hz), 7.38 (1H, d, J=8.3 Hz), 6.63 (1H, d, J=8.5 Hz), 3.59 (2H, s), 2.44 (2H, s), 2.32 (3H, s), 0.90-0.81 (4H, m) ESI-MS Found: m/z [M+H]+ 494.

Preparative Example 2-1

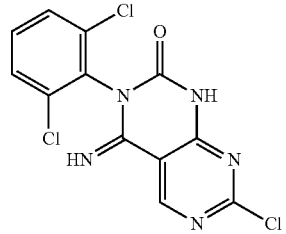 [SMILES: N=c1c2cnc(Cl)nc2[nH]c(=O)n1-c1c(Cl)cccc1Cl]

Production of 7-chloro-3-(2,6-dichlorophenyl)-4-imino-3,4-dihydropyrimido[4,5-d]pyrimidin-2(1H)-one 1.12 g of sodium hydride was added to an N,N-dimethylformamide (35 mL) solution of 3.0 g of 4-amino-2-chloropyrimidine-5-carbonitrile, and stirred at room temperature for 5 minutes. 4.38 g of 2,6-dichlorophenyl isocyanate was added to the reaction liquid, and stirred at room temperature for 1 hour. Ethyl acetate and aqueous 1 N hydrochloric acid solution were added to the reaction solution, and the organic layer was separated. This was washed with saturated saline water, dried with anhydrous magnesium sulfate, and the solvent was evaporated away. The precipitated solid was solidified with a mixed solvent of methanol/ethyl acetate and taken out through filtration to obtain the entitled compound as a white solid. $^1$H-NMR (400 MHz, DMSO-d$_6$) δ: 9.33 (1H, s), 7.66 (2H, d, J=8.2 Hz), 7.53 (1H, t, J=8.2 Hz) ESI-MS Found: m/z [M+H] 342.

Preparative Example 2-2

Production of 2'-methyl-2',3'-dihydro-1'H-spiro[cyclopropane-1,4'-isoquinolin]-7'-amine

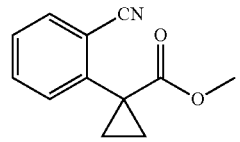

Step 1) Production of methyl 1-(2-cyanophenyl)cyclopropanecarboxylate 1.5 g of tetra-n-butylammonium bromide, 6.5 g of 1,2-dibromoethane and 20 mL of aqueous 50% sodium hydroxide solution were added to a toluene (40 mL) solution of 4.0 g of methyl 2-cyanophenylacetate, and stirred at room temperature for 1 hour. Water was added to the reaction liquid, and extracted with ethyl acetate. The organic layer was washed with saturated saline water, dried with anhydrous magnesium sulfate, and the solvent was evaporated away under reduced pressure. The crude product was purified through silica gel column chromatography (hexane/ethyl acetate) to obtain the entitled compound as a colorless compound. $^1$H-NMR (400 MHz, CDCl$_3$) δ: 7.66 (1H, dd, J=7.6, 1.2 Hz), 7.55 (1H, td, J=7.6, 1.2 Hz), 7.43-7.36 (2H, m), 3.66 (3H, s), 1.82 (2H, q, J=3.7 Hz), 1.30 (2H, q, J=3.7 Hz) ESI-MS Found: m/z [M+H] 202

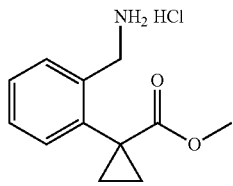

Step 2) Production of methyl 1-[2-(aminomethyl)phenyl]cyclopropanecarboxylate monohydrochloride 1.6 g of 10% palladium-carbon was added to an ethanol (50 mL) solution of 2.95 g of the compound obtained in the above reaction Step 1), and stirred in a hydrogen atmosphere under 2 atmospheric pressure at room temperature for 3 hours. The palladium-carbon was removed through filtration, the filtrate was concentrated under reduced pressure, and the crude product was washed with diethyl ether to obtain the entitled compound as a colorless solid. $^1$H-NMR (DMSO-$d_6$) δ: 8.47 (2H, s), 7.55 (1H, d, J=6.8 Hz), 7.38 (3H, td, J=7.2, 2.1 Hz), 7.36-7.29 (2H, m), 4.04 (2H, d, J=4.9 Hz), 3.54 (3H, s), 1.61-1.56 (2H, m), 1.33-1.29 (2H, m) ESI-MS Found: m/z [M+H] 206.

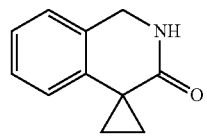 [SMILES: O=C1NCc2ccccc2C12CC2]

Step 3) Production of 1',2'-dihydro-3'H-spiro[cyclopropane-1,4'-isoquinolin]-3'-one 4 mL of aqueous 5 N sodium hydroxide solution was added to a methanol (50 mL) solution of 3.2 g of the compound obtained in the above reaction Step 2), and stirred at room temperature for 30 minutes. This was neutralized with aqueous 1 N hydrochloric acid added thereto, and methanol was evaporated away under reduced pressure. The residue was diluted with water, and extracted three times with ethyl acetate. The organic layer was washed with saturated saline water, dried with anhydrous magnesium sulfate, and the solvent was evaporated away under reduced pressure to obtain the entitled compound as a colorless solid. $^1$H-NMR (CDCl$_3$) δ: 7.23 (1H, td, J=7.8, 1.1 Hz), 7.18 (1H, td, J=7.3, 1.1 Hz), 7.10 (1H, dd, J=7.3, 1.0 Hz), 6.73 (1H, dd, J=7.8, 1.0 Hz), 4.69 (2H, d, J=1.5 Hz), 1.85 (2H, q, J=3.7 Hz), 1.24 (2H, q, J=3.7 Hz) ESI-MS Found: m/z [M+H] 174.

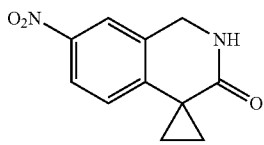 [SMILES: O=C1NCc2cc([N+](=O)[O-])ccc2C12CC2]

Step 4) Production of 7'-nitro-1',2'-dihydro-3'H-spiro[cyclopropane-1,4'-isoquinolin]-3'-one 1.3 g of potassium nitrate was gradually added to a sulfuric acid (60 mL) solution of 2.1 g of the compound obtained in the above reaction 3), taking 5 minutes, and further stirred at room temperature for 10 minutes. The reaction liquid was poured into ice water, the precipitated crystal was taken out through filtration, and washed with water to obtain the entitled compound as a yellow solid. $^1$H-NMR (CDCl$_3$) δ: 8.09 (1H, dd, J=8.8, 2.4 Hz), 8.01 (1H, t, J=2.4 Hz), 6.86 (1H, d, J=8.8 Hz), 6.30 (1H, s), 4.78 (2H, d, J=1.5 Hz), 2.01 (2H, q, J=4.1 Hz), 1.35 (2H, q, J=4.1 Hz) ESI-MS Found: m/z [M+H] 219.

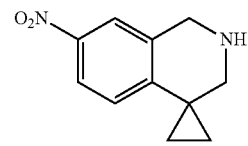

Step 5) Production of 7'-nitro-1',2'-dihydro-3'H-spiro[cyclopropane-1,4'-isoquinoline]

With cooling with ice, 6.3 g of boron trifluoride-diethyl ether complex was added to a tetrahydrofuran suspension of 1.3 g of sodium borohydride, and stirred for 1 hour. A tetra-hydrofuran (100 ml) solution of 2.4 g of the compound obtained in the above reaction Step 4) was added to the reaction liquid, and heated under reflux for 2 hours. The reaction liquid was cooled, and then neutralized with aqueous saturated sodium bicarbonate solution. The solvent was evaporated away under reduced pressure, the residue was dissolved in ethanol, 5 N hydrochloric acid was added to it, and heated under reflux for 1 hour. The reaction liquid was cooled, then the solvent was evaporated away under reduced pressure, and the residue was neutralized with aqueous potassium carbonate solution. The aqueous layer was extracted with chloroform, the organic layer was dried with anhydrous magnesium sulfate, and the solvent was evaporated away under reduced pressure to obtain the entitled compound. ESI-MS Found: m/z [M+H] 205.

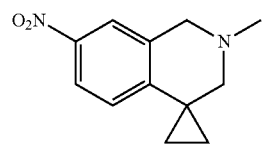

Step 6) Production of 2'-methyl-7'-nitro-2',3'-dihydro-1'H-spiro[cyclopropane-1,4'-isoquinoline]

1.5 g of sodium cyanoborohydride was added to a methanol (50 mL) solution of the compound (2.3 g) obtained in the above reaction Step 5), 2.7 mL of aqueous 37% formaldehyde solution and 0.7 mL of acetic acid, and stirred at room temperature for 15 hours. The reaction liquid was neutralized with aqueous saturated sodium bicarbonate solution, and methanol was evaporated away under reduced pressure. The residue was diluted with water and extracted three times with chloroform. The organic layer was dried with anhydrous magnesium sulfate, the solvent was evaporated away under reduced pressure, and the crude product was purified through silica gel column chromatography (hexane/ethyl acetate) to obtain the entitled compound as a colorless solid. $^1$H-NMR (CDCl$_3$) δ: 7.97 (1H, dd, J=8.8, 2.4 Hz), 7.91 (1H, d, J=2.4 Hz), 6.78 (1H, d, J=8.8 Hz), 3.77 (2H, s), 2.57 (2H, s), 2.48 (3H, s), 1.16-1.12 (2H, m), 1.10-1.06 (2H, m) ESI-MS Found: m/z [M+H] 219.

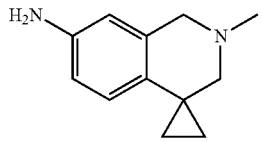 [SMILES: CN1Cc2cc([N+](=O)[O-])ccc2C2(CC2)C1]

Step 7) Production of 2'-methyl-2',3'-dihydro-1'H-spiro[cyclopropane-1,4'-isoquinolin]-7'-amine 800 mg of 10% palladium-carbon was added to an ethanol (20 mL) solution of 1.7 g of the compound obtained in the above reaction Step 6), and stirred in a hydrogen atmosphere under 1 atmospheric pressure at room temperature for 15 hours. Palladium-carbon was removed through filtration, the filtrate was concentrated under reduced pressure, and the crude product was purified through basic silica gel column chromatography (hexane/ethyl acetate) to obtain the entitled compound as a colorless solid. $^1$H-NMR (CDCl$_3$) δ: 6.50-6.48 (2H, m), 6.38-6.36 (1H, m), 3.61 (2H, s), 3.50 (2H, s), 2.49 (2H, s), 2.42 (3H, s), 0.91 (2H, dd, J=6.3, 4.6 Hz), 0.81 (2H, dd, J=6.3, 4.6 Hz) ESI-MS Found: m/z [M+H] 189.

Example 3

General Materials and Methods

A. Cell Culture, Proliferation Assays, and MYT1 siRNA Knockdown

All cancer cell lines were grown in medium recommended by the cell line vendor (ATCC). Tissue culture media, serum, and supplements were purchased from Sigma-Aldrich® (St. Louis, Mo.). For the proliferation assay screen (FIG. 1), cells were plated in 384-well tissue culture plates and grown under compound or vehicle treatment. After 96 hours, CellTiter-Glo (Promega, Madison, Wis.) was used according to the manufacturer's protocol to approximate cell content. Samples were run in triplicate and growth was calculated as the CellTiter-Glo raw value of treated samples relative to vehicle-treated control wells.

For the knockdown studies, NCI-H460 and KNS62, two non-small cell lung cancer cell lines, American Type Culture Collection, Manassas, Va., were transfected with siRNA pools (SMARTpool, Dharmacon, Thermo Fisher Scientific, Waltham, Mass.) with either non-targeting control or PKMYT1 sequences. Cells were seeded 48 hours after transfection in 96-well tissue culture plates and the next day they were treated with compound or vehicle for 72 hours. To approximate cell content, ViaLight (Lonza, Basel, Switzerland) was used according to manufacturer's protocol. Samples were run in triplicate and growth was calculated by determining the percentage of the control raw value for each treatment.

B. Western Blotting

Cells were lysed in mammalian protein extraction reagent (MPER, Thermo Fisher 78505, Waltham, Mass.) and then subjected to SDS-PAGE and transferred onto nitrocellulose or PVDF membranes. Antibodies used for Western blotting are from the following sources: total CDK1, pCDK1$^{Y15}$, pCDK1$^{T14}$, pCHK1$^{S345}$, pStathmin$^{S38}$, pLaminA/C$^{S22}$, pCDK substrate motif, γH2AX, Cyclin A, and total PKMYT1 from Cell Signaling Technologies (Beverly, Mass.); actin-HRP from Santa Cruz Biotechnology (Santa Cruz, Calif.); secondary HRP-conjugated anti-mouse and rabbit antibodies from GE Healthcare (Waukesha, Wis.). Blots were exposed with SuperSignal West Femto chemiluminescent substrate (Thermo Fisher Pierce, Waltham, Mass.).

C. Flow Cytometry

To detect DNA double strand breaks, cells were stained with a FITC-conjugated anti-γH2AX (S139) antibody (kit 17-344, Millipore, Billerica, Mass.) after having been fixed overnight in ice-cold 70% ethanol Propidium iodide (PI)/RNase solution (BD Biosciences, Franklin Lakes, N.J.) was used to detect total DNA content. For studies interrogating premature mitosis, an anti-pHH3-Alexa 647 antibody (BD Biosciences 558217) was added.

For synchronization studies, cells were incubated in serum-free medium for 36 hours, followed by replenishment with 20% FBS. One hour prior to each harvest, cells were pulsed with 10 μM bromodeoxyuridine (BrdU). Cells were fixed and stained for BrdU and DNA content with an anti-BrdU FITC-conjugated antibody and 7-aminoactinomycin-D (7-AAD) dye, respectively, according to the instructions in the BD Pharmingen™ FITC BrdU Flow Kit (BD Biosciences, Franklin Lakes, N.J.). All cytometry data were collected on the BD LSR II flow cytometer using the BD FACS Diva™ software (BD Biosciences, Franklin Lakes, N.J.), and the results were analyzed in FlowJo version 7.5.

D. In Vivo Efficacy Studies

CD-1 Nu/Nu female mice aged 5-6 weeks were obtained from Charles River Laboratories (Wilmington, Del.) and housed in Applicants animal care facility at standard laboratory conditions and fed 2018S autoclaveable diet (Harlan Laboratories, Indianapolis, Ind.) and water ad libitum. The protocol was approved by Applicants' in-house animal care and use committee. Mice were inoculated with cells (1:1 Matrigel:PBS) subcutaneously (SC) into the right flank. When tumor volume reached 200 mm$^3$ (+1-50) mice were pair-matched so each group had a similar mean and standard deviation. Tumor volume and body weights were recorded bi-weekly. Mice received four treatment cycles of twice daily dosing (BID) for two days, receiving either vehicle or WEE1-1 (60 mpk).

Example 4

Inhibition of WEE1 Disrupts Cell Proliferation in Diverse Tumor Cell Lines

Loss of WEE1 expression in mice through gene targeting is lethal, disrupting development even before embryos reach the blastocyst stage (pre-embryonic day 3.5). This phenotype is caused by apoptosis and premature mitoses in embryos as well as DNA damage in mouse embryonic fibroblasts lacking the WEE1 gene (Tominaga, Y., et al., *J. Biol. Sciences,* 2006, 2(4):161-170). Additionally, RNAi-mediated silencing of WEE1 leads to impaired viability in numerous transformed human cell lines. WEE1-1 is a potent ATP-competitive inhibitor of WEE1 and sensitizes cancer cells to exogenous DNA damage (Hirai, H., et al., *Mol. Cancer Ther.,* 2009, 8(11):2992-3000). Applicants used this small molecule inhibitor to investigate the effects of pharmacological inhibition of WEE1 across a diverse panel of human tumor cell lines (FIG. 1).

A wide array of responses was observed when 522 cancer lines, representing 16 different tumor types, were screened with WEE1-1 in a cellular proliferation assay (FIG. 1). $EC_{50}$ values ranged from ≤0.1 µM in 2% (9/522) to ≥1 µM in 19% (98/522) for the cell lines tested. Comparing mean $EC_{50}$ values of the different tumor types revealed that, as a group, colorectal cancer cell lines were less sensitive (mean $EC_{50}$=1.16 µM, n=66, range 0.17 to >10 µM) and neuroblastoma tumor cell lines were on average more sensitive to WEE1-1 treatment (mean $EC_{50}$=0.28 µM, n=7, range 0.12 to 0.45 µM). The sample size of the latter group was limited, but the finding that neuroblastoma cells tend to be more responsive to WEE1 inhibition is consistent with recent findings (Russell et al., submitted manuscript). It was notable that many cell lines continue to grow and divide even with the presence of higher concentrations of WEE1-1. These data demonstrated the anti-proliferative potential of pharmacologic WEE1 inhibition and the diversity among humor tumor cell lines.

Example 5

WEE1 Inhibition Activates the DNA Damage Response

Figure 2A:
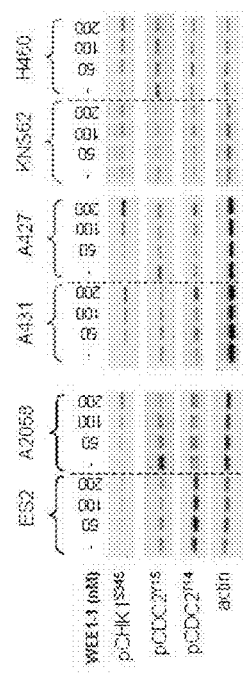
FIGS. 2A and 2B are illustrations of the DNA damage in S phase resulting from treatment with a WEE1 inhibitor, wherein ES-2, A2058, A431, A427, KNS62, and NCI-H460 cells were treated with either DMSO (−) or increasing concentrations of WEE1-1 for 2 hours. Protein lysates were analyzed by Western blotting with antibodies against phosphorylated $CHK1^{S345}$, phosphorylated $CDK1^{Y15}$, phosphorylated $CDK1^{T14}$, or actin as a loading control (FIG. 2A). TOV-21G cells were treated with DMSO or 150 nM WEE1-1 for up to 2 or 6 hours (FIG. 2B). Cells were pulse-labeled one hour prior to harvest with BrdU to label S phase cells actively undergoing DNA replication. Cells were analyzed by flow cytometry for DNA double strand breaks (γH2AX) versus total DNA content (FIG. 2B, left panels) or γH2AX versus BrdU uptake (FIG. 2B, right panels). The percentage of γH2AX-staining cells represents the cell population containing DNA double strand breaks and is indicated for each treatment condition and separated by BrdU status in the right panels.
Figure 8A:
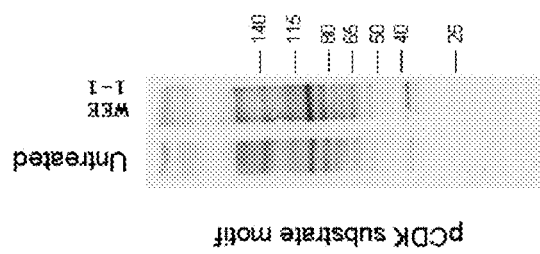
FIGS. 8A and 8B illustrate that inhibition of WEE1 by WEE1-1 leads to increased CDK1 and 2 activity. ES-2 cells were treated for 24 hours with either DMSO or 250 nM WEE1-1, collected, and lysed for Western blot analysis.
Figure 8B:
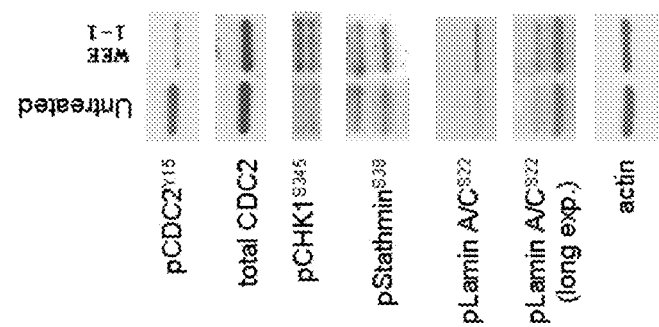

Functional genomic screens and validation studies have demonstrated that knockdown of WEE1 leads to DNA double strand breaks and activation of the DNA damage response (DDR). Applicants used $pCHK1^{S345}$ as a marker of activated DDR to examine the effect of pharmacologic inhibition of WEE1 in six cell lines of varying sensitivity to WEE1-1: ES-2 ($EC_{50}$=256 nM), A2058 ($EC_{50}$=225 nM), A431 ($EC_{50}$=170 nM), A427 ($EC_{50}$=116 nM), KNS62 ($EC_{50}$=487 nM), and NCI-H460 ($EC_{50}$=535 nM). Western blots for $pCHK1^{S345}$ demonstrated a dose-dependent activation of the DDR in all six cell lines and evidence of increased $pCHK1^{S345}$ with as little as 50 nM WEE1-1 in the more sensitive cell lines, i.e., ES-2, A2058, A431, and A427 (FIG. 2A). Elevated CDK activity as a result of WEE1-1 treatment was confirmed in ES-2 cells (FIG. 8A). As expected, an accompanying dose-dependent reduction in $pCDK1^{Y15}$ was also observed in all six cell lines, providing a link between induction of the DDR and elevated CDK activity as a result of WEE1 inhibition. Phosphorylation of CDK1 and CDK2 at T14 by PKMYT1 is also known to impair CDK1/2 kinase activity and WEE1-1 inhibits PKMYT1 in vitro at roughly 100-fold higher concentrations that those required to inhibit WEE1 (Hirai, H., et al., 2009). Applicants questioned whether $pCDK1^{T14}$ levels were affected by WEE1-1 concentrations that induced DNA damage. With the possible exception of the A427 cell line, Applicants did not observe a WEE1-1-dependent effect on $pCDK1^{T14}$ (FIG. 2A).

Example 6

WEE1 Inhibition Disrupts S-Phase Dynamics and DNA Replication Integrity

Figure 2B:
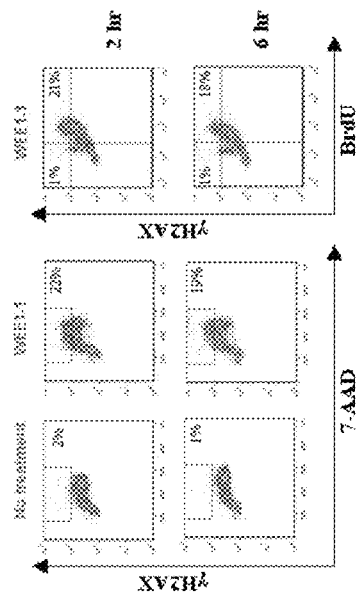

To understand where WEE1-1-dependent DNA damage takes place, Applicants analyzed TOV21G ovarian cancer cells by flow cytometry. In exponentially growing TOV21G cells, 1% to 2% of the population stained positive for the DNA double strand break marker γH2AX. However, as little as two hours of treatment with WEE1-1 resulted in 23% of cells staining positive for the γH2AX (FIG. 2B, left panel). Chromosomal content of the γH2AX positive cells was >2N, suggesting that DNA damage arising from WEE1 inhibition occurs during or after the initiation of DNA replication in S-phase. When TOV21G cells were treated with WEE1-1 and pulse-labeled with BrdU, DNA damage was detected almost exclusively in BrdU-positive cells (95% at 2 hours, 92% at 6 hours) which supports Applicants' observation that DNA double strand breaks are a consequence of WEE1 inhibition during DNA replication (FIG. 2B, right panel).

Figure 3A:
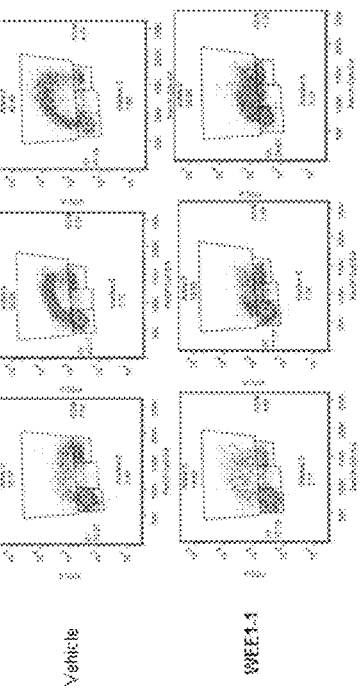
FIGS. 3A-3C are illustration of the delays in S phase progression resulting from treatment with a WEE1 inhibitor. ES-2 cells were synchronized following 36 hours serum withdrawal.
Figure 3B:
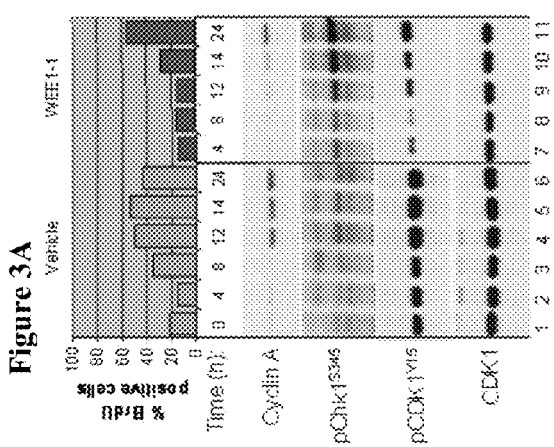
Figure 3C:
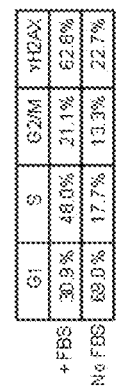
Figure 9B:
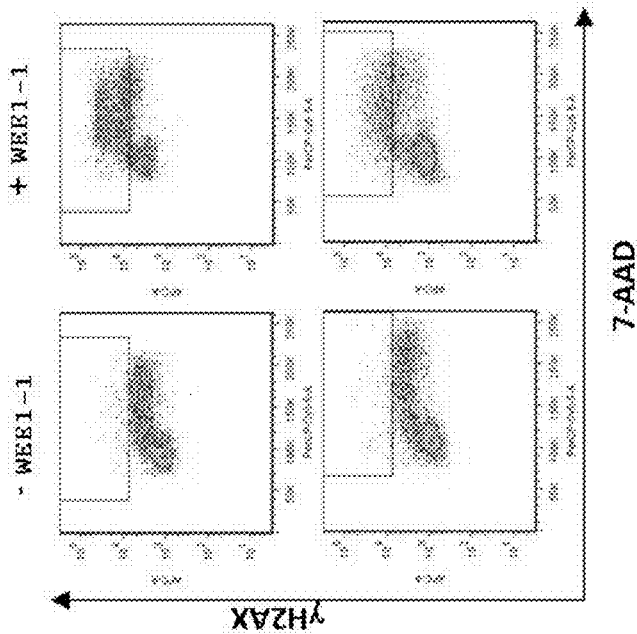
FIGS. 9A and 9B illustrate that DNA damage, induced by WEE1-1 treatment, requires mitogen stimulation. ES-2 cells were serum starved for 36 hours at which point they were either left unstimulated or treated with 20% FBS. Cells cultured under both conditions received either DMSO or 500 nM WEE1-1 for 24 hours before collection for flow cytometry analysis of DNA content (7-AAD) and DNA double strand breaks (γH2AX).
Figure 9A:
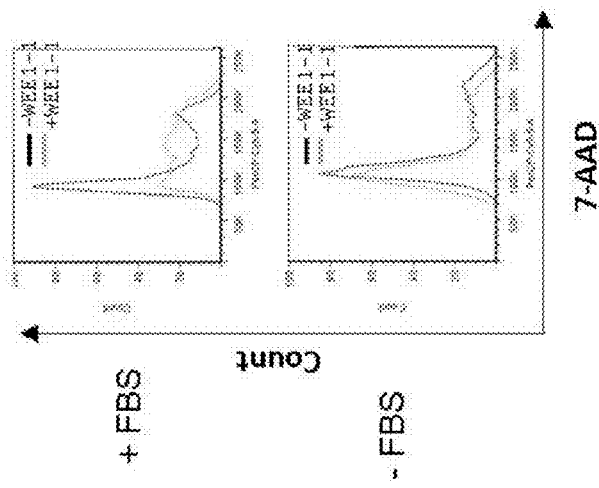

Chromosomal breaks in S-phase were expected to activate the DNA replication checkpoint and slow progression through S-phase. Cell synchronization studies were carried out to confirm this expectation. ES-2 cell lines were selected for these studies because they were more amenable than other cell lines to G1 synchronization induced by mitogen withdrawal upon serum depletion (data not shown). Other approaches to S-phase synchronization (e.g. double-thymidine block, aphidicolin, hydroxyurea, actinomycin D, etc.) were not utilized because these methods can independently induce DNA damage and be disruptive to the dynamics of DNA replication. As shown in FIG. 3A, serum withdrawal for 36 hours did not completely arrest ES-2 cells in G1. However, the addition of 20% FBS caused vehicle-treated ES-2 cells to double their S-phase population to about 40% by 8 hours and peak at 50% by 12 to 14 hours. In contrast, when WEE1-1 treatment was included with the addition of 20% FBS, there was no detectable change in the S-phase population by 8 hours and peak levels (about 50%) were delayed until 24 hours post-FBS (FIG. 3A). Even at its peak, the mean fluorescent intensity of incorporated BrdU was far lower in WEE1-1 as compared to vehicle-treated cells, suggestive of slowed DNA replication in the BrdU positive population. Western blot analysis presented in FIG. 3A confirmed the delayed S-phase progression (cyclin A), a more rapid and robust activation of the DDR ($pCHK1^{S345}$), and inhibition of WEE1 kinase activity ($pCDK1^{Y15}$) in WEE1-1-treated relative to vehicle-treated cells. Interestingly, phosphorylation of $pCDK1^{Y15}$ increased over the 24 hour time course in ES-2 cells. The degree of DNA double strand breaks (γH2AX) induced by 24 hours of WEE1-1 treatment was appreciably larger under conditions of mitogen stimulation where a sharp increase of DNA replication was observed as compared to cells that were not restimulated (FIG. 3B and FIG. 9).

Example 7

DNA Damage as the Primary Cytotoxic Consequence of WEE1 Inhibition

Figure 4:
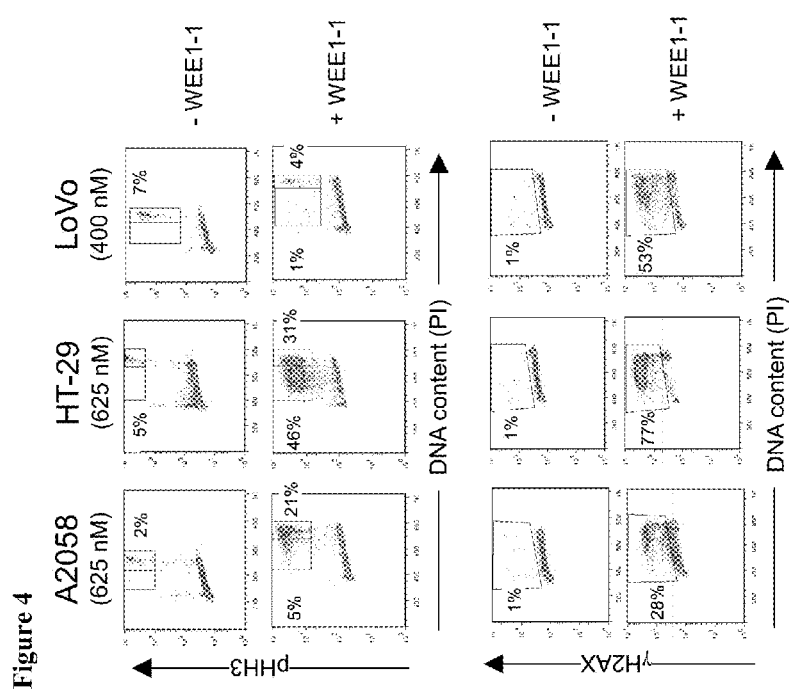
FIGS. 4A and 4B illustrate that premature mitosis is not necessary to induce cytotoxicity with WEE1 inhibition. A2058, HT-29, and LoVo cells were treated for 24 hours with either DMSO (−WE 1-1) or WEE1-1 at $EC_{90}$ concentrations of the drug. Flow cytometry was used to identify the population of cells positive for the mitotic marker phosphorylated histone H3 ($pHH3^{S10}$, FIG. 4A) or the DNA double strand break marker γH2AX (FIG. 4B). In the upper panels, the gate on the right indicates the expected mitotic population (4N DNA content) and the gate on the left indicates cells positive for pHH3 with less than 4N DNA content.

WEE1 is required for the temporal activation of both CDK2 and CDK1 kinases in S and G2 phases of the cell cycle, respectively Inhibition of WEE1, therefore, was expected to lead to S phase defects (DNA double strand breaks during DNA replication) and G2-M defects (premature mitosis). To assess whether either or both of these effects is necessary or sufficient for sensitivity to WEE1-1, γH2AX and phosphorylated histone H3 (pHH3), a marker of mitosis, at cytotoxic ($EC_{90}$ concentrations of WEE1-1 was examined in three sensitive cell lines, A2058, HT-29, and LoVo. After 24 hours of treatment with WEE1-1, the percentage of pHH3 positive cells had increased in all three cell lines (FIG. 4). Of the three lines, only the HT-29 cells contained a substantial mitotic population, 43% with 4N DNA and 23% with <4N DNA, which indicates premature mitosis from S-phase cells had not completed DNA replication. However, a substantial H2AX-positive cell population was observed in all three cell lines following WEE1-1 treatment (8% in A2058, 59% in HT-29, 27% in LoVo). Without wishing to be bound by any theory, these data suggest that induction of DNA double strand breaks (γH2AX) rather than premature mitosis (pHH3) was the primary cytotoxic consequence of WEE1 inhibition by WEE1-1 in sensitive cell lines.

Example 8

Anti-Tumor Activity In Vivo from WEE1 Inhibition

Figure 5:
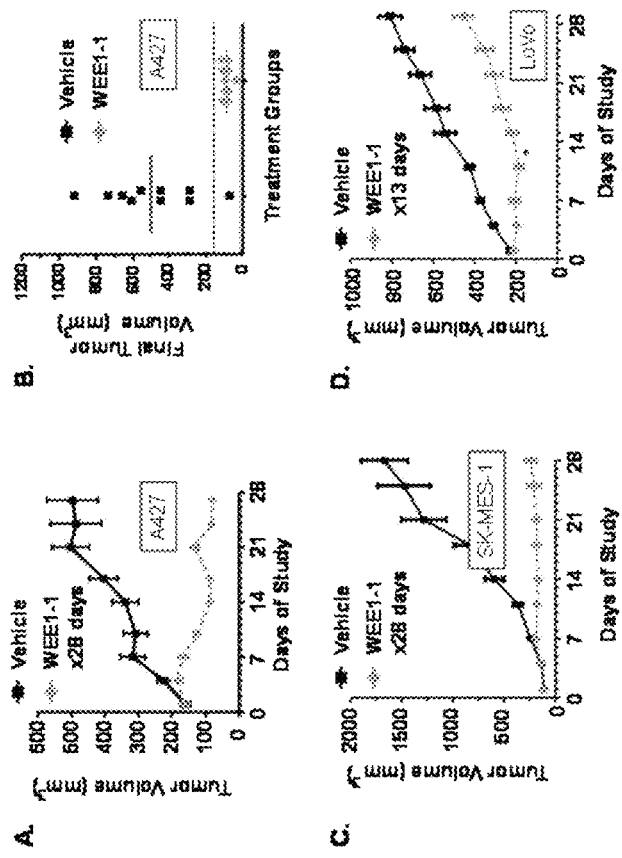
FIGS. 5A-5D are illustrations of in vivo efficacy of WEE1-1 single agent treatment, in which A427 xenograft bearing mice were dosed with either vehicle (0.5% methylcellulose) or 60 mg/kg of WEE1-1. Dosing of both vehicle and compound was BID for 28 consecutive days. Xenograft tumor volumes were taken twice weekly and plotted (mean volume−/+SEM) against days of treatment for vehicle (n=10) and WEE1-1 (n=10) treated mice (FIG. 5A).

To determine the effect of WEE1-1 monotherapy treatment on tumor growth in vivo at tolerated doses, a maximum tolerated dose (MTD) was established at 60 mg per kg for twice daily (BID) dosing. Mean body weight loss over the course of a 28-day study at this dose and schedule did not exceed 5% in the treated group (data not shown). WEE1-1 inhibited proliferation in the A427 non-small cell lung cancer cell line at low concentrations ($EC_{50}$=116 nM) and readily induced the DNA damage response (FIG. 2A). In the A427 xenograft model, WEE1-1 treatment caused regression to approximately 50% of the initial mean tumor volume (FIG. 5A). Individual tumor analysis showed that 9 out of the 10 vehicle treated A427 tumors grew between 2- to 6-fold over their starting volume (FIG. 5B). In contrast, the final volumes for all 10 WEE1-1 treated tumors were smaller than their initial volumes (FIG. 5B). Anti-tumor growth effects of WEE1-1 single agent treatment were observed in additional xenograft models (FIG. 5C): Tumor growth inhibition (TGI) was 92% in the SK-MES-1 NSCLC model, 13% tumor regression in a LoVo colorectal tumor model, 88% TGI in an A431 epidermoid tumor model, and 64% TGI in a NCI-H2122 NSCLC model. The percent TGI was calculated as 100−(100* ΔT/ΔC) if ΔT>0 where ΔT=final mean volume−initial mean volume of treated group and AC=final mean volume−initial mean volume of vehicle control group. Collectively these data demonstrated the anti-tumor therapeutic potential of WEE1 inhibition at well tolerated doses of WEE1-1.

Example 9

PKMYT1 Expression Affected Sensitivity to WEE1 Inhibitor

WEE1 expression is essential for embryonic viability (Tominaga, Y., et al., 2006) and the majority of cancer cell lines screened show at least some degree of sensitivity to treatment with WEE1-1 (FIG. 1). However, not all cell lines were equally susceptible to WEE1 inhibition and the anti-proliferative $EC_{50}$s ranged at least 10-fold (FIG. 1). Applicants have found herein that a potential determinant of sensitivity to WEE1 inhibition is the activity of a functionally related CDK-inhibitory kinase, PKMYT1. Phosphorylation of CDK1 or CDK2 at either of two N-terminal sites, T14 or Y15, caused inactivation of this kinase despite the presence of an otherwise activating cyclin binding partner (cyclin B or cyclin A, respectively). WEE1 is known to phosphorylate Y15 of CDK1 and CDK2, and PKMYT1 has been shown to similarly inhibit CDK1 and CDK2 through phosphorylation at T14 and/or Y15 (Mueller, P. R., et al., Science, 1995, 270(5233):86-90).

Figure 6A:
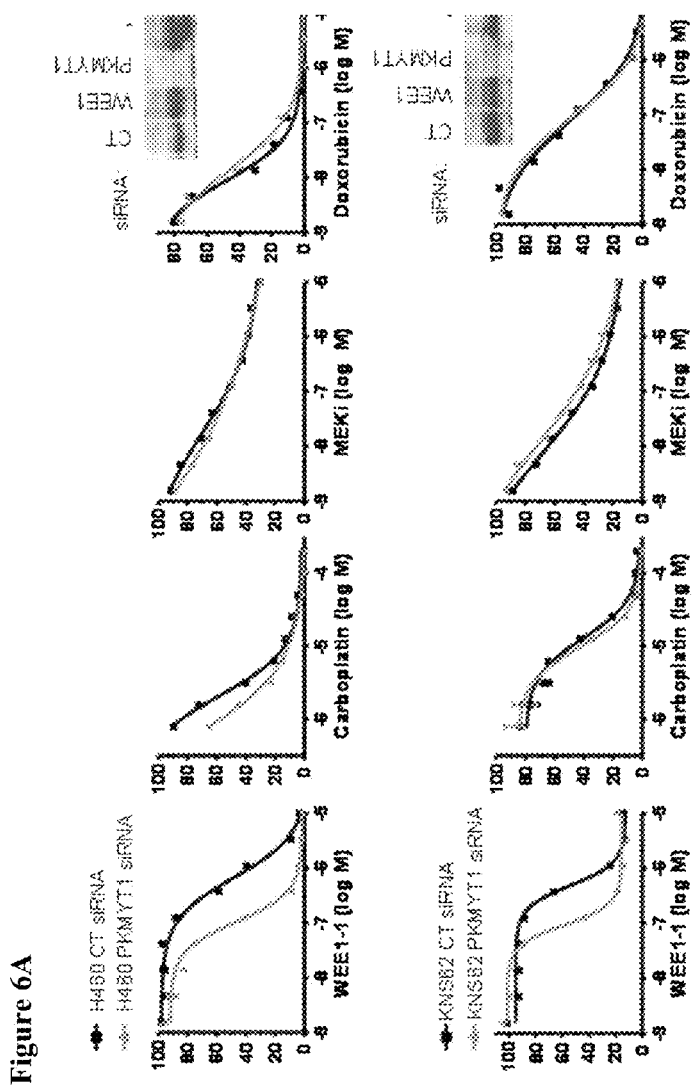
FIGS. 6A and 6B illustrate that PKMYT1 knockdown selectively increased sensitivity to WEE1-1 and reduced inhibitory phosphorylation of CDK1.
Figure 6B:
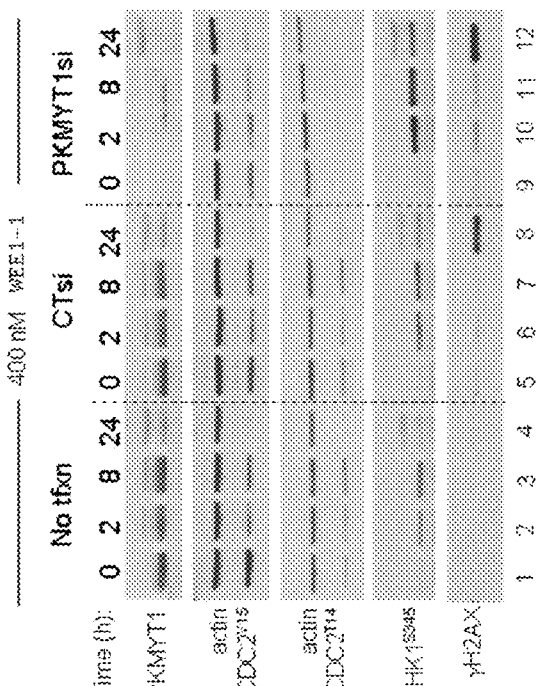

Applicants herein used siRNA knockdown to evaluate whether PKMYT1 expression can specifically alter the response to WEE1 inhibition in two cell lines, NCI-H460 and KNS62. These lines were selected because they demonstrate relative insensitivity to WEE1-1 treatment and have relatively high expression of PKMYT1 (data not shown). Cells were transfected with a pool of four distinct siRNAs, all targeting PKMYT1, and analyzed in proliferation assays for sensitivity to different cytotoxic agents (FIG. 6A). As illustrated in FIG. 6A, The WEE1-1 anti-proliferative $EC_{50}$s for NCI-H460 (n=3) and KNS62 (n=2) shifted from 677 nM to 104 nM and from 487 nM to 93 nM, respectively, when PKMYT1 was knocked down. Notably, the maximal effect of WEE1-1 treatment was not affected by PKMYT1 depletion. Using the fold-change in $EC_{50}$ as a measure of potentiation, PKMYT1 potentiated WEE1-1 an average of 4.7-fold in NCI-H460 cells (n=3) and 4.9-fold in KNS62 cells (n=2). The specificity of PKMYT1-dependent sensitization to WEE1-1 was confirmed by identical dose response curves in both the control (CT) and PKMYT1 siRNA transfected cells treated with carboplatin, a MEK inhibitor (PD-0325901), or doxorubicin (FIG. 6A). Western blot analysis of KNS62 cells (FIG. 6B) indicated that PKMYT1 knockdown resulted in slightly lower basal phosphorylation of CDK1 and 2 on Y15 and markedly reduced basal phosphorylation on T14 (lane 9 versus lanes 1 and 5). Knockdown of PKMYT1 also lead to an overall increase in both pCHK1$^{S345}$ and γH2AX. This was consistent with the observations that WEE1-1-mediated cytotoxicity resulted from DNA damage (FIGS. 4A and 4B) and that PKMYT1. knockdown increased sensitivity to WEE1-1 and its anti-proliferative effect (FIG. 6B).

Figure 7A:
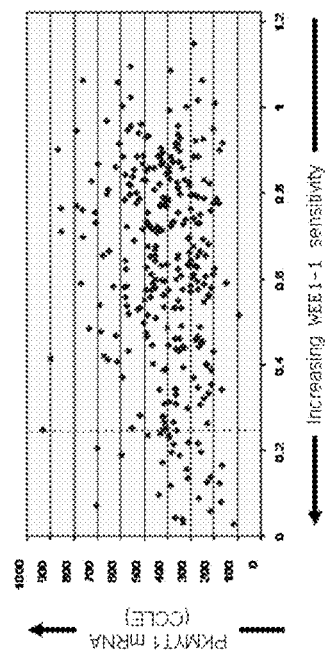
FIGS. 7A and 7B illustrate that low PKMYT1 expression enhanced sensitivity to WEE1-1.

In that PKMYT1. knockdown lead to increased sensitivity to WEE1-1, Applicants hypothesized that low PKMYT1 expression may also be predictive of the most WEE1-1-responsive cell lines. To validate this hypothesis, a 522 cell line panel for PKMYT1 mRNA levels was evaluated using the Broad-Novartis Cancer Cell Line Encyclopedia (CCLE), a publicly available cell line database, of the collaboration between the Broad Institute (Cambridge, Mass.) and the Novartis Institute for Biomedical Research (Cambridge, Mass.) and its Genomics Institute of the Novartis Research Foundation (San Diego, Calif.) (Stransky, B. C., et al., *Nature*, 2012, 483:603-807). Of the 522 cancer cell lines assayed for sensitivity to WEE1-1, expression data for PKMYT1 was available for 305 lines. A plot of the relative PKMYT1. expression from the CUE database against the observed cell line response data at 450 nM of WEE1-1 did not demonstrate a correlation between PKMYT1 mRNA and WEE1-1 sensitivity (FIG. 7A). However, 24 of the 33 cell lines (73%) that were killed when treated with WEE1-1 at 450 nM (response<0.25 on an adjusted scale, indicated by dashed line in FIG. 7A) had less than the mean expression level, i.e., 413±154, for PKMYT1 mRNA.

Figure 7B:
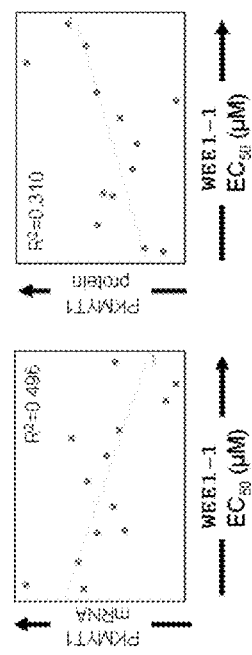

To further test the hypothesis that PKMYT1 expression was predictive of WEE1-1 sensitivity, 13 additional cell lines were selected from the CCLE database that had not previously been treated with WEE1-1. The anti-proliferative $EC_{50}$ values for WEE1-1 in these 13 cell lines correlated to both mRNA expression (FIG. 7B, left panel) and protein levels (FIG. 7B, right panel) of PKMYT1. Taken together these data support the hypothesis that low PKMYT1 expression was predictive of WEE1-1 responsive cell lines, i.e. sensitivity to treatment with WEE1-1.

What is claimed:

1. A method for treating a patient diagnosed with a WEE1 kinase associated cancer with a WEE1 inhibitor comprising:
   (a) measuring the gene expression level of PKMYT1 in a biological sample comprising cancer cells obtained from said patient and in a control sample;
   (b) determining whether the gene expression level in said patient sample is above or below the level of that in said control sample;
   (c) selecting said patient for treatment with a WEE1 inhibitor, wherein the level of PKMYT1 from said patient sample is below that of the control sample; and
   (d) administering a WEE1 inhibitor to the selected patient.

2. The method according to claim 1, wherein said control sample is obtained from one or more subjects who are disease free or who have not been diagnosed with a WEE1 kinase associated cancer.

3. The method according to claim 1, wherein said WEE1 inhibitor is WEE1-1, or a pharmaceutically acceptable salt thereof, or WEE1-2, or a pharmaceutically acceptable salt thereof.

4. The method according to claim 3, wherein said WEE1 inhibitor is WEE1-1 or a pharmaceutically acceptable salt thereof.

5. The method according to claim 3, wherein said WEE1 inhibitor is WEE1-2 or a pharmaceutically acceptable salt thereof.

6. A method for treating a cancer patient sensitive to treatment with a WEE1 inhibitor comprising:
   (a) measuring the gene expression level of PKMYT1 in a biological sample comprising cancer cells obtained from said patient and in a control sample;
   (b) determining whether the gene expression level in said patient sample is above or below the level of that in said control sample;
   (c) identifying said sensitive patient for treatment with a WEE1 inhibitor, wherein the level of PKMYT1 from said patient sample is below that of the control sample; and
   (d) administering a WEE1 inhibitor to the sensitive patient.

7. The method according to claim 6, wherein said control sample is obtained from one or more subjects who are disease free or who have not been diagnosed with a WEE1 kinase associated cancer.

8. The method according to claim 6, wherein said WEE1 inhibitor is WEE1-1, or a pharmaceutically acceptable salt thereof, or WEE1-2, or a pharmaceutically acceptable salt thereof.

9. The method according to claim 8, wherein said WEE1 inhibitor is WEE1-1 or a pharmaceutically acceptable salt thereof.

10. The method according to claim 8, wherein said WEE1 inhibitor is WEE1-2 or a pharmaceutically acceptable salt thereof.

11. The method according to claim 6, wherein said cancer is a WEE1 kinase associated cancer selected from the group consisting of breast cancer, lung cancer, pancreatic cancer, colon cancer, ovarian cancer, acute leukemia, chronic lymphatic leukemia, chronic myelocytic leukemia, and Hodgkin's lymphoma.

* * * * *